United States Patent [19]
Jautelat et al.

[11] Patent Number: 6,114,539
[45] Date of Patent: Sep. 5, 2000

[54] MERCAPTO-IMIDAZOLYL DERIVATIVES

[75] Inventors: Manfred Jautelat, Burscheid; Ralf Tiemann, Leverkuesen; Stefan Dutzmann, Langenfeld; Klaus Stenzel, Düsseldorf, all of Germany

[73] Assignee: Bayer Aktiengesellschaft, Leverkusen, Germany

[21] Appl. No.: 09/180,909

[22] PCT Filed: May 9, 1997

[86] PCT No.: PCT/EP97/02374

§ 371 Date: Nov. 17, 1998

§ 102(e) Date: Nov. 17, 1998

[87] PCT Pub. No.: WO97/44323

PCT Pub. Date: Nov. 27, 1997

[30] Foreign Application Priority Data

May 21, 1996 [DE] Germany ............... 196 20 408

[51] Int. Cl.⁷ .................. C07D 233/84; A01N 43/50
[52] U.S. Cl. .............. 548/323.5; 514/341; 514/383; 514/397; 514/399; 514/400; 546/274.4; 248/268.6; 248/311.1; 248/315.4; 248/315.7; 248/325.1; 248/329.5
[58] Field of Search ............ 548/325.1, 311.1, 548/329.5, 268.6; 514/399, 400; 546/274.4

[56] References Cited

U.S. PATENT DOCUMENTS

| | | | |
|---|---|---|---|
| 3,912,752 | 10/1975 | Meiser et al. | 260/308 R |
| 3,952,002 | 4/1976 | Kramer et al. | 260/308 R |
| 4,048,318 | 9/1977 | Meiser et al. | 424/269 |
| 4,079,062 | 3/1978 | Van Reet et al. | 260/308 R |
| 4,147,791 | 4/1979 | Meiser et al. | 424/269 |
| 4,205,075 | 5/1980 | Baldwin et al. | 424/269 |
| 4,243,405 | 1/1981 | Balasubramanyan et al. | 471/76 |
| 4,464,381 | 8/1984 | Janssen et al. | 424/269 |
| 4,532,341 | 7/1985 | Holmwood et al. | 549/559 |
| 4,549,900 | 10/1985 | Krämer et al. | 71/92 |
| 4,598,085 | 7/1986 | Heeres et al. | 514/383 |
| 4,626,595 | 12/1986 | Holmwood et al. | 549/559 |
| 4,652,580 | 3/1987 | Janssen et al. | 514/383 |
| 4,723,984 | 2/1988 | Holmwood et al. | 71/76 |
| 4,789,672 | 12/1988 | Holmwood et al. | 514/184 |
| 4,871,390 | 10/1989 | Holmwood et al. | 71/92 |
| 4,897,107 | 1/1990 | Holmwood et al. | 71/92 |
| 4,904,297 | 2/1990 | Holmwood et al. | 71/92 |
| 4,906,652 | 3/1990 | Karbach et al. | 514/383 |
| 4,911,746 | 3/1990 | Holmwood et al. | 71/92 |
| 4,913,727 | 4/1990 | Stroech et al. | 514/184 |
| 4,952,232 | 8/1990 | Cuomo et al. | 71/92 |
| 4,965,280 | 10/1990 | Cuomo et al. | 514/383 |
| 4,965,281 | 10/1990 | Cuomo et al. | 514/399 |
| 4,968,712 | 11/1990 | Elbe et al. | 514/383 |
| 4,980,488 | 12/1990 | Stroech et al. | 549/563 |
| 4,988,819 | 1/1991 | Stroech et al. | 548/267.8 |
| 4,990,677 | 2/1991 | Stroech et al. | 548/29 |
| 5,034,052 | 7/1991 | Stroech et al. | 71/92 |
| 5,081,141 | 1/1992 | Colle et al. | 514/383 |
| 5,084,465 | 1/1992 | Cuomo et al. | 514/341 |
| 5,087,635 | 2/1992 | Shaber | 514/383 |
| 5,097,047 | 3/1992 | Stroech et al. | 549/463 |
| 5,256,683 | 10/1993 | Hutt et al. | 514/383 |
| 5,266,585 | 11/1993 | Hubele et al. | 514/383 |
| 5,380,743 | 1/1995 | Hutt et al. | 514/399 |
| 5,639,918 | 6/1997 | Hutt et al. | 568/329 |
| 5,789,430 | 8/1998 | Jautlat et al. | 514/272.4 |

FOREIGN PATENT DOCUMENTS

| | | | |
|---|---|---|---|
| 015 756 | 9/1980 | European Pat. Off. | |
| 0 052 424 | 5/1982 | European Pat. Off. | |
| 0125033 | 11/1984 | European Pat. Off. | 548/325.1 |
| 044 605 | 2/1986 | European Pat. Off. | |
| 0221778 | 5/1987 | European Pat. Off. | 548/325.1 |
| 061 835 | 2/1989 | European Pat. Off. | |
| 0308573 | 3/1989 | European Pat. Off. | 548/325.1 |
| 145 294 | 10/1989 | European Pat. Off. | |
| 267 778 | 3/1993 | European Pat. Off. | |
| 195 20 095 | 12/1996 | Germany. | |
| 98/01267 | 2/1988 | WIPO | 548/325.1 |

OTHER PUBLICATIONS

Chemical Abstracts, vol. 89, No. 13, Sep. 25, 1978, Abstract No. 109238 M.V. Postyanoi et al.

*Primary Examiner*—Floyd D. Higel
*Attorney, Agent, or Firm*—Joseph C. Gil; Carol Marmo

[57] ABSTRACT

The present invention provides mercapto-imidazolyl compounds, and the acid addition salts and metal salt complexes thereof; a process for their preparation; and a method for their use as microbicides.

9 Claims, No Drawings

MERCAPTO-IMIDAZOLYL DERIVATIVES

TECHNICAL FIELD OF THE INVENTION

The present invention relates to new mercapto-imidazolyl derivatives, to a plurality of processes for their preparation, and to their use as microbicides.

BACKGROUND OF THE INVENTION

It has already been disclosed that a large number of imidazolyl derivatives have fungicidal properties (cf. EP-A 0 015 756, EP-A 0 040 345, EP-A 0 052 424, EP-A 0 061 835, EP-A 0 297 345, EP-A 0 094 564, EP-A 0 196 038, EP-A 0 267 778, EP-A 0 378 953, EP-A 0 044 605, EP-A 0 069 442, EP-A 0 055 833, EP-A 0 301 393, DE-A 2 324 010, DE-A 2 737 489, DE-A 2 551 560, EP-A 0 065 485, DE-A 2 735 872, EP-A 0 234 242, DE-A 2 201 063, EP-A 0 145 294 and DE-A 3 721 786). While the activity of these substances is good, it leaves something to be desired in some cases at low rates of application.

DETAILED DESCRIPTION OF THE INVENTION

There have now been found new mercapto-imidazolyl derivatives of the formula

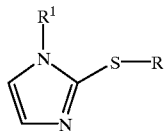

(I)

in which
R represents hydrogen or alkyl having 1 to 4 carbon atoms and
$R^1$ represents a radical of the formula

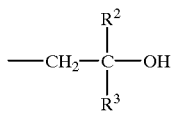

where
$R^2$ and $R^3$ are identical or different and represent optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl,
or
$R^1$ represents a radical of the formula

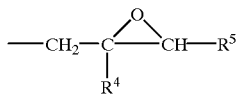

where
$R^4$ represents alkyl having 1 to 4 carbon atoms, halogenoalkyl having 1 to 4 carbon atoms and 1 to 5 halogen atoms, cycloalkyl having 3 to 7 carbon atoms which is optionally substituted by halogen, or represents naphthyl, or represents phenyl which is optionally monosubstituted to trisubstituted by identical or different substituents from the series consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and/or halogenoalkylthio having 1 to 4 carbon atoms and 1 to 5 halogen atoms, and $R^5$ represents phenyl which is optionally monosubstituted to trisubstituted by identical or different substituents from the series consisting of halogen, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and/or halogenoalkylthio having 1 to 4 carbon atoms and 1 to 5 halogen atoms,
or
$R^1$ represents a radical of the formula

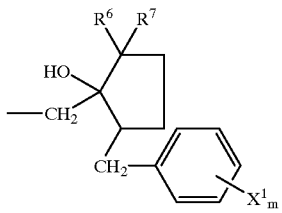

where
$R^6$ and $R^7$ independently of one another represent hydrogen or alkyl having 1 to 6 carbon atoms,
$X^1$ represents halogen, alkyl having 1 to 5 carbon atoms, alkoxy having 1 to 4 carbon atoms, phenyl, phenoxy, halogenoalkyl having 1 to 4 carbon atoms and 1 to 5 halogen atoms, halogenoalkoxy having 1 to 4 carbon atoms and 1 to 5 halogen atoms, or represents halogenoalkylthio having 1 to 4 carbon atoms and 1 to 5 halogen atoms, and
m represents the numbers 0, 1 or 2,
or
$R^1$ represents a radical of the formula

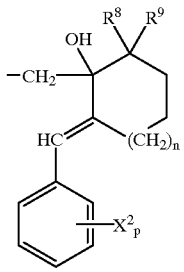

where
$R^8$ and $R^9$ independently of one another represent hydrogen or alkyl having 1 to 6 carbon atoms,
$X^2$ represents halogen, cyano, nitro, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to halogen atoms, or phenyl,
n represents the numbers 0 or 1, and p represents the numbers 0, 1 or 2,
or
$R^1$ represents a radical of the formula

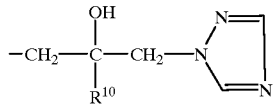

where
$R^{10}$ represents alkyl having 1 to 6 carbon atoms, halogenoalkyl having 1 to 6 carbon atoms and 1 to 5 halogen atoms, cycloalkyl having 3 to 6 carbon atoms which is optionally substituted by halogen and/or alkyl having 1 to 4 carbon atoms, or represents optionally substituted aryl, or represents optionally substituted aralkyl,
or
$R^1$ represents a radical of the formula

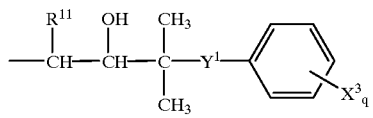

where
$R^{11}$ represents hydrogen, alkyl or optionally substituted cycloalkyl,
$X^3$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms,
q represents the numbers 0, 1, 2 or 3 and
$Y^1$ represents an oxygen atom, a $CH_2$ group or a direct bond,
or
$R^1$ represents a radical of the formula

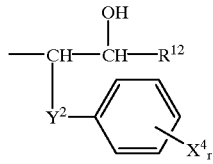

where
$R^{12}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, or represents cycloalkylalkyl having 3 to 7 carbon atoms in the cycloalkyl moiety and 1 to 4 carbon atoms in the alkyl moiety, or represents phenyl which is optionally substituted by halogen, or represents benzyl which is optionally substituted by halogen,
$X^4$ represents halogen, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms,
r represents the numbers 0, 1, 2 or 3 and
$Y^2$ represents an oxygen atom or a $CH_2$ group,
or
$R^1$ represents a radical of the formula

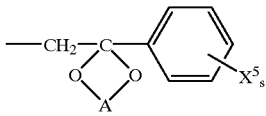

where
A represents alkanediyl having 2 or 3 carbon atoms which is optionally substituted by halogen and/or alkyl having 1 to 4 carbon atoms,
$X^5$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms,
and
s represents the numbers 0, 1, 2 or 3,
or
$R^1$ represents a radical of the formula

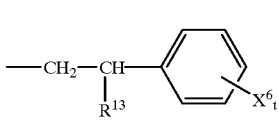

where
$R^{13}$ represents alkyl having 1 to 10 carbon atoms, halogenoalkyl having 1 to 6 carbon atoms and 1 to 5 halogen atoms, fluoroalkoxyalkyl having 1 to 4 carbon atoms in the fluoroalkoxy moiety and 1 to 4 carbon atoms in the alkyl moiety, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, phenyl which is optionally substituted by halogen, or phenylalkyl which has 1 to 4 carbon atoms in the alkyl moiety and is optionally substituted by halogen,
$X^6$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms, and
t represents the numbers 0, 1, 2 or 3, or $R^1$ represents a radical of the formula

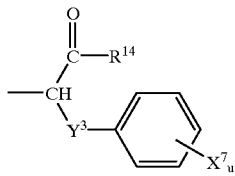

where $R^{14}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, phenyl which is optionally substituted by halogen or benzyl which is optionally substituted by halogen, $X^7$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms, u represents the numbers 0, 1, 2 or 3 and $Y^3$ represents an oxygen atom or a $CH_2$ group, or $R^1$ represents a radical of the formula

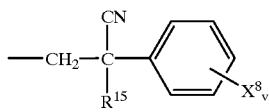

where $R^{15}$ represents alkyl having 1 to 6 carbon atoms, halogenoalkyl having 1 to 6 carbon atoms and 1 to 5 halogen atoms, optionally substituted aryl or optionally substituted aralkyl, $X^8$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms and v represents the numbers 0, 1, 2 or 3, and their acid addition salts and metal salt complexes.

A large number of substances according to the invention comprise one or more asymmetrically substituted carbon atoms. They can therefore be obtained in the form of optical isomers. The present invention relates to the individual isomers and also to mixtures of these.

Furthermore, it has been found that mercapto-imidazolyl derivatives of the formula (I) and their acid addition salts and metal salt complexes are obtained when imidazoles of the formula

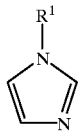

(II)

in which $R^1$ has the abovementioned meanings are either a) reacted in succession with strong bases and sulphur in the presence of a diluent and the product is then hydrolysed with water, if appropriate in the presence of an acid, or b) reacted with sulphur in the presence of a diluent of high boiling point and, if appropriate, the product is then treated with water and, if appropriate, with acid, and the compounds of the formula

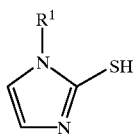

(Ia)

in which $R^1$ has the abovementioned meanings which are formed by variants (a) and (b), are, if appropriate, reacted with halogen compounds of the formula $$R^{16}—HaI \qquad (III)$$

in which $R^{16}$ represents alkyl having 1 to 4 carbon atoms and

HaI represents chlorine, bromine or iodine in the presence of an acid binder and in the presence of a diluent, and, if appropriate, the resulting compounds of the formula (I) are subsequently subjected to an addition reaction with an acid or a metal salt.

Finally, it has been found that the new mercapto-imidazolyl derivatives of the formula (I) and their acid addition salts and metal salt complexes have very good microbicial properties and can be employed both in crop protection and in the protection of materials.

Surprisingly, the substances according to the invention have a better microbicidal activity than the prior-art compounds of the same direction of action which are most similar constitutionally.

Formula (I) provides a general definition of the mercapto-imidazolyl derivatives according to the invention.

R preferably represents hydrogen, methyl, ethyl, n-propyl or isopropyl.

$R^1$ preferably represents a radical of the formula

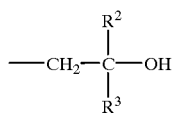

in which
$R^2$ preferably represents straight-chain or branched alkyl having 1 to 6 carbon atoms, it being possible for these radicals to be monosubstituted to tetrasubstituted by identical or different substituents from the series consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, it being possible for each of these radicals to be monosubstituted to trisubstituted by identical or different substituents from the series consisting of halogen, alkoxy having 1 to 4 carbon atoms and/or cycloalkyl having 3 to 7 carbon atoms, or represents cycloalkyl having 3 to 7 carbon atoms, it being possible for each of these radicals to be monosubstituted to trisubstituted by identical or different substituents from the series consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, it being possible for the aryl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, it being possible for the aryl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, it being possible for the aryl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, it being possible for each of these radicals to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused, five- or six-membered heteroaromatic radical having 1 to 3 hetero atoms such as nitrogen, sulphur and/or oxygen, it being possible for each of these radicals to be monosubstituted to trisubstituted by identical or different substituents from the series consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano, and $R^3$ preferably represents straight-chain or branched alkyl having 1 to 6 carbon atoms, it being possible for these radicals to be monosubstituted to tetrasubstituted by identical or different substituents from the series consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, it being possible for each of these radicals to be monosubstituted to trisubstituted by identical or different substituents from the series consisting of halogen, alkoxy having 1 to 4 carbon atoms and/or cycloalkyl having 3 to 7 carbon atoms, or represents cycloalkyl having 3 to 7 carbon atoms, it being possible for each of these radicals to be monosubstituted to trisubstituted by identical or different substituents from the series consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, it being possible for the aryl moiety to be in each case monosubstituted to trisubstituted by identical or different substituents from the series consisting of halogen atoms, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, it being possible for the aryl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, it being possible for the aryl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, it being possible for each of these radicals to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused, five- or six-membered heteroaromatic radical having 1 to 3 hetero atoms such as nitrogen, sulphur and/or oxygen, it being possible for each of these radicals to be monosubstituted to trisubstituted by identical or different substituents from the series consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano.

$R^1$ furthermore preferably represents a radical of the formula

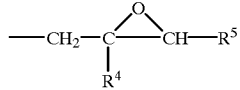

in which $R^4$ preferably represents methyl, ethyl, n-propyl, isopropyl, n-butyl, sec-butyl, iso-butyl, tert-butyl, fluoro-tert-butyl, difluoro-tert-butyl, cycloalkyl having 3 to 6 carbon atoms which is optionally monosubstituted to trisubstituted by identical or different substituents from the series consisting of fluorine, chlorine and/or bromine, or represents naphthyl, or represents phenyl which can be monosubstituted to trisubstituted by identical or different substituents from the series consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and/or trifluoromethylthio, and $R^5$ preferably represents phenyl which can be monosubstituted to trisubstituted by identical or different substituents from the series consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and/or trifluoromethylthio.

$R^1$ furthermore preferably represents a radical of the formula

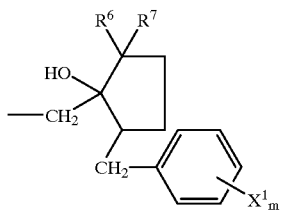

in which $R^6$ preferably represents hydrogen, methyl, ethyl, n-propyl, isopropyl, n-butyl, isobutyl, sec-butyl, tert-butyl or n-pentyl, $R^7$ preferably represents hydrogen, methyl, ethyl, n-propyl, isopropyl, n-butyl, isobutyl, sec-butyl, tert-butyl or n-pentyl, $X^1$ preferably represents fluorine, chlorine, bromine, methyl, ethyl, n-propyl, isopropyl, n-butyl, isobutyl, sec-butyl, tert-butyl, methoxy, ethoxy, phenyl, phenoxy, trichloromethyl, trifluoromethyl, trifluoromethoxy, difluoromethoxy or trifluoromethylthio and m also preferably represents the numbers 0, 1 or 2,
it being possible for $X^1$ to represent identical or different radicals if m represents 2.

$R^1$ furthermore preferably represents a radical of the formula

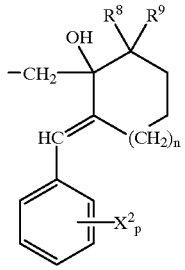

in which $R^8$ preferably represents hydrogen, methyl, ethyl, n-propyl, isopropyl, n-butyl, isobutyl, sec-butyl, tert-butyl or n-pentyl, $R^9$ preferably represents hydrogen, methyl, ethyl, n-propyl, isopropyl, n-butyl, isobutyl, sec-butyl, tert-butyl or n-pentyl, $X^2$ preferably represents fluorine, chlorine, bromine, cyano, nitro, methyl, ethyl, n-propyl, isopropyl, n-butyl, isobutyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also preferably represents the numbers 0 or 1 and p also preferably represents the numbers 0, 1 or 2,
it being possible for $X^2$ to represent identical or different radicals if p represents 2.

$R^1$ furthermore preferably represents a radical of the formula

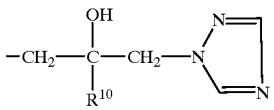

in which $R^{10}$ preferably represents straight-chain or branched alkyl having 1 to 4 carbon atoms, straight-chain or branched halogenoalkyl having 1 to 4 carbon atoms and 1 to 5 fluorine, chlorine and/or bromine atoms, cycloalkyl having 3 to 6 carbon atoms which is optionally monosubstituted to trisubstituted by identical or different substituents from the series consisting of fluorine, chlorine, bromine, methyl and/or ethyl, or represents phenyl, benzyl or phenethyl, it being possible for each of the three last-mentioned radicals to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or phenoxy which is optionally substituted by halogen and/or alkyl having 1 to 4 carbon atoms.

$R^1$ furthermore preferably represents a radical of the formula

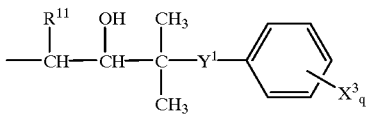

in which $R^{11}$ preferably represents hydrogen, straight-chain or branched alkyl having 1 to 12 carbon atoms, or cycloalkyl having 3 to 7 carbon atoms which is optionally monosubstituted to trisubstituted by identical or different substituents from the series consisting of halogen and/or alkyl having 1 to 4 carbon atoms, $X^3$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy, q preferably represents the numbers 0, 1, 2 or 3, $X^3$ representing identical or different radicals if q represents 2 or 3, and $Y^1$ preferably represents an oxygen atom, a $CH_2$ group or a direct bond.

$R^1$ furthermore preferably represents a radical of the formula

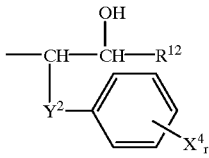

in which $R^{12}$ preferably represents straight-chain or branched alkyl having 1 to 4 carbon atoms, fluoroalkyl having 1 to 4 carbon-atoms and 1 to 5 fluorine atoms, cycloalkyl having 3 to 6 carbon atoms which is optionally mono-substituted to trisubstituted by identical or different substituents from the series consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally monosubstituted to trisubstituted by identical or different substituents from the series consisting of fluorine, chlorine and/or bromine, or benzyl which is optionally monosubstituted to trisubstituted by identical or different substituents from the series consisting of fluorine, chlorine and/or bromine, $X^4$ preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl which is optionally monosubstituted or disubstituted by identical or different substituents from the series consisting of fluorine, chlorine, bromine and/or methyl, or phenoxy which is optionally monosubstituted or disubstituted by identical or different substituents from the series consisting of fluorine, chlorine, bromine and/or methyl, r preferably represents the numbers 0, 1, 2 or 3, $X^4$ representing identical or different radicals if r represents 2 or 3, and $Y^2$ preferably represents an oxygen atom or a $CH_2$ group.

$R^1$ furthermore preferably represents a radical of the formula

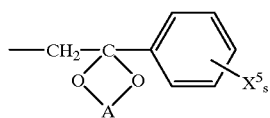

in which

A preferably represents alkanediyl having 2 or 3 carbon atoms which is optionally monosubstituted to trisubstituted by identical or different substituents from the series consisting of fluorine, chlorine, bromine, methyl, ethyl, n-propyl, isopropyl, n-butyl, i-butyl, sec-butyl and/or tert-butyl, $X^5$ preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally monosubstituted to trisubstituted by identical or different substituents from the series consisting of fluorine, chlorine and/or methyl, and/or phenoxy which is optionally monosubstituted to trisubstituted by identical or different substituents from the series consisting of fluorine, chlorine and/or methyl, and s preferably represents the numbers 0, 1, 2 or 3, $X^5$ representing identical or different radicals if s represents 2 or 3.

$R^1$ furthermore preferably represents a radical of the formula

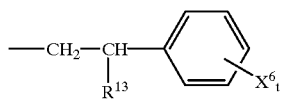

in which $R^{13}$ preferably represents straight-chain or branched alkyl having 1 to 6 carbon atoms, straight-chain or branched halogenoalkyl having 1 to 6 carbon atoms and 1 to 5 fluorine, chlorine and/or bromine atoms, fluoroalkoxyalkyl having 1 to 3 carbon atoms and 1 to 5 fluorine atoms in the fluoroalkoxy moiety and 1 to 3 carbon atoms in the alkyl moiety, cycloalkyl having 3 to 6 carbon atoms which is optionally monosubstituted to trisubstituted by identical or different substituents from the series consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally monosubstituted to trisubstituted by identical or different substituents from the series consisting of fluorine, chlorine and/or bromine, or phenylalkyl having 1 or 2 carbon atoms in the alkyl moiety which is optionally monosubstituted to trisubstituted by identical or different substituents from the series consisting of fluorine, chlorine and/or bromine, $X^6$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally monosubstituted or disubstituted by identical or different substituents from the series consisting of fluorine, chlorine, bromine and/or methyl, or phenoxy which is optionally monosubstituted or disubstituted by identical or different substituents from the series consisting of fluorine, chlorine, bromine and/or methyl, and t preferably represents the numbers 0, 1, 2 or 3, $X^6$ representing identical or different radicals if t represents 2 or 3.

$R^1$ further-more preferably represents a radical of the formula

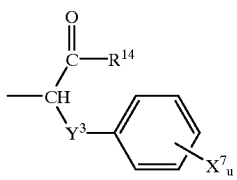

in which $R^{14}$ preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally monosubstituted to trisubstituted by identical or different substituents from the series consisting of fluorine, chlorine, bromine, methyl and/or ethyl, cycloalkylalkyl having 3 to 6 carbon atoms in the cycloalkyl moiety and 1 to 3 carbon atoms in the alkyl moiety, phenyl which is optionally monosubstituted to trisubstituted by identical or different substituents from the series consisting of fluorine, chlorine and/or bromine, or benzyl which is optionally monosubstituted to trisubstituted by identical or different substituents from the series consisting of fluorine, chlorine and/or bromine, $X^7$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally monosubstituted or disubstituted by identical or different substituents from the series consisting of fluorine, chlorine, bromine and/or methyl, or phenoxy which is optionally monosubstituted or disubstituted by identical or different substituents from the series consisting of fluorine, chlorine, bromine and/or methyl, u preferably represents the numbers 0, 1, 2 or 3, $X^7$ representing identical or different radicals if u represents 2 or 3, and $Y^3$ preferably represents an oxygen atom or a $CH_3$ group.

Moreover, $R^1$ also preferably represents a radical of the formula

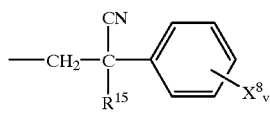

in which $R^{15}$ preferably represents straight-chain or branched alkyl having 1 to 4 carbon atoms, halogenoalkyl having 1 to 4 carbon atoms and 1 to 5 halogen atoms, phenyl which is optionally monosubstituted to trisubstituted by identical or different substituents from the series consisting of halogen, alkyl having 1 to 4 carbon atoms, halogenoalkyl having 1 or 2 carbon atoms having 1 to 5 halogen atoms, alkoxy having 1 to 4 carbon atoms and/or halogenoalkoxy having 1 or 2 carbon atoms and 1 to 5 halogen atoms, or represents phenylalkyl having 1 to 4 carbon atoms in the alkyl moiety which is optionally monosubstituted to trisubstituted by identical or different substituents from the series consisting of halogen, alkyl having 1 to 4 carbon atoms, halogenoalkyl having 1 or 2 carbon atoms and 1 to 5 halogen atoms, alkoxy having 1 to 4 carbon atoms and/or halogenoalkoxy having 1 or 2 carbon atoms and 1 to 5 halogen atoms, $X^8$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally monosubstituted or disubstituted by identical or different substituents from the series consisting of fluorine, chlorine, bromine and/or methyl, or phenoxy which is optionally monosubstituted or disubstituted by identical or different substituents from the series consisting of fluorine, chlorine, bromine and/or methyl, and v preferably represents the numbers 0, 1, 2 or 3, $X^8$ representing identical or different radicals if v represents 2 or 3.

R especially preferably represents hydrogen, methyl or ethyl.

$R^1$ especially preferably represents a radical of the formula

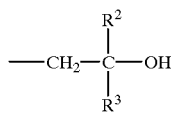

in which $R^2$ especially preferably represents straight-chain or branched alkyl having 1 to 4 carbon atoms, it being possible for these radicals to be monosubstituted to tetrasubstituted by identical or different substituents from the series consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, it being possible for each of these radicals to be monosubstituted to trisubstituted by identical or different substituents from the series consisting of fluorine, chlorine, bromine, methoxy, ethoxy, propoxy, isopropoxy, cyclopropyl, cyclobutyl, cyclopentyl and/or cyclohexyl, or represents cycloalkyl having 3 to 6 carbon atoms, it being possible for each of these radicals to be monosubstituted to trisubstituted by identical or different substituents from the series consisting of fluorine, chlorine, bromine, cyano, methyl, ethyl, propyl, isopropyl and/or tert-butyl, or represents phenylalkyl having 1 to 4 carbon atoms in the straight-chain or branched alkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methyoximinoethyl, nitro and/or cyano, or represents phenylalkenyl having 2 to 4 carbon atoms in the alkenyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/ or cyano, or represents phenoxyalkyl having 1 to 4 carbon atoms in the straight-chain or branched oxyalkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/ or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl, and $R^3$ especially preferably represents straight-chain or branched alkyl having 1 to 4 carbon atoms, it being possible for these radicals to be monosubstituted to tetrasubstituted by identical or different substituents from the series consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, it being possible for each of these radicals to be monosubstituted to trisubstituted by identical or different substituents from the series consisting of fluorine, chlorine, bromine, methoxy, ethoxy, propoxy, isopropoxy, cyclopropyl, cyclobutyl, cyclopentyl and/or cyclohexyl, or represents cycloalkyl having 3 to 6 carbon atoms, it being possible for each of these radicals to be monosubstituted to trisubstituted by identical or different substituents from the series consisting of fluorine, chlorine, bromine, cyano, methyl, ethyl, propyl, isopropyl and/or tert-butyl, or represents phenylalkyl having 1 to 4 carbon atoms in the straight-chain or branched alkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenylalkenyl having 2 to 4 carbon atoms in the alkenyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenoxyalkyl having 1 to 4 carbon atoms in the straight-chain or branched oxyalkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be monosubstituted to be trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl.

$R^1$ furthermore especially preferably represents a radical of the formula

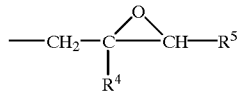

in which $R^4$ especially preferably represents methyl, ethyl, n-propyl, isopropyl, n-butyl, sec-butyl, iso-butyl, tert-butyl, fluoro-tert-butyl, difluoro-tert-butyl, cycloalkyl having 3 to 6 carbon atoms which is optionally monosubstituted to trisubstituted by identical or different substituents from the series consisting of fluorine, chlorine and/or bromine, or represents naphthyl, or represents phenyl which can be monosubstituted to trisubstituted by identical or different substituents from the series consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and/or trifluoromethylthio, and $R^5$ especially preferably represents phenyl which can be monosubstituted to trisubstituted by identical or different substituents from the series consisting of fluorine, chlorine, bromine, methyl, ethyl, isopropyl, tert-butyl, methoxy, ethoxy, trifluoromethyl, trichloromethyl, difluoromethyl, difluorochlormethyl, trifluoromethoxy, difluoromethoxy and/or trifluoromethylthio.

$R^1$ furthermore especially preferably represents a radical of the formula

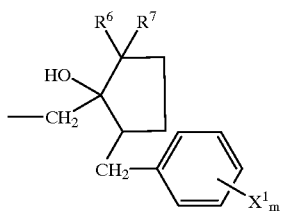

in which

R[6] especially preferably represents hydrogen, methyl, ethyl, n-propyl, isopropyl, n-butyl, iso-butyl, sec-butyl, tert-butyl or n-pentyl, R[7] especially preferably represents hydrogen, methyl, ethyl, n-propyl, isopropyl, n-butyl, iso-butyl, sec-butyl, tert-butyl or n-pentyl, $X^1$ especially preferably represents fluorine, chlorine, bromine, methyl, ethyl, n-propyl, isopropyl, n-butyl, iso-butyl, sec-butyl, tert-butyl, methoxy, ethoxy, phenyl, phenoxy, trichloromethyl, trifluoromethyl, trifluoromethoxy, difluoromethoxy or trifluoromethylthio, and m also especially preferably represents the numbers 0, 1 or 2, it being possible for $X^1$ to represent identical or different radicals if m represents 2.

$R^1$ furthermore especially preferably represents a radical of the formula

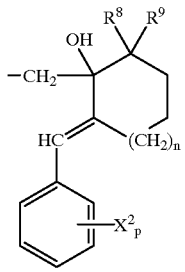

in which

R[8] especially preferably represents hydrogen, methyl, ethyl, n-propyl, isopropyl, n-butyl, iso-butyl, sec-butyl, tert-butyl or n-pentyl, R[9] especially preferably represents hydrogen, methyl, n-propyl, isopropyl, n-butyl, iso-butyl, sec-butyl, tert-butyl or n-pentyl, $X^2$ especially preferably represents fluorine, chlorine, bromine, cyano, nitro, methyl, ethyl, n-propyl, isopropyl, n-butyl, iso-butyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also especially preferably represents the numbers 0 or 1 and p also especially preferably represents the numbers 0, 1 or 2, it being possible for $X^2$ to represent identical or different radicals if p represents 2.

$R^1$ furthermore especially preferably represents a radical of the formula

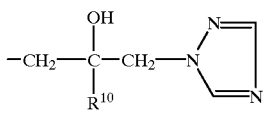

in which

R[10] especially preferably represents methyl, ethyl, n-propyl, isopropyl, n-butyl, sec-butyl, iso-butyl, tert-butyl, halogenoalkyl having 1 to 4 carbon atoms and 1 to 3 fluorine, chlorine and/or bromine atoms, cyclopropyl, cyclopentyl or cyclohexyl, each of which is optionally monosubstituted to trisubstituted by identical or different substituents from the series consisting of fluorine, chlorine, bromine, methyl and/or ethyl, and represents phenyl, benzyl or phenethyl, it being possible for each of the three last-mentioned radicals to be monosubstituted to trisubstituted in the phenyl moiety by identical or different substituents from the series consisting of fluorine, chlorine, bromine, methyl, ethyl, methoxy, methylthio, trichloromethyl, trifluoromethyl, trifluoromethoxy, difluoromethoxy, trifluoromethylthio, phenyl and/or phenoxy.

$R^1$ furthermore especially preferably represents a radical of the formula

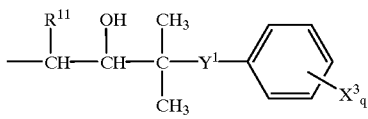

in which

R[11] especially preferably represents hydrogen, straight-chain or branched alkyl having 1 to 6 carbon atoms, or cyclopropyl, cyclopentyl or cyclohexyl, each of which is optionally monosubstituted to trisubstituted by identical or different substituents from the series consisting of fluorine, chlorine, bromine, methyl and/or ethyl, $X^3$ especially preferably represents fluorine, chlorine, bromine, methyl, methoxy, methylthio, trichloromethyl, trifluoromethyl, trifluoromethoxy, difluoromethoxy, trifluoromethylthio, phenyl or phenoxy, q also especially preferably represents the numbers 0, 1, 2 or 3, $X^3$ representing identical or different radicals if q represents 2 or 3 and $Y^1$ also especially preferably represents an oxygen atom, a $CH_2$ group or a direct bond.

$R^1$ furthermore especially preferably represents a radical of the formula

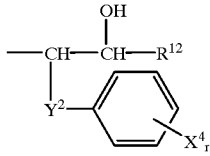

in which

R[12] especially preferably represents methyl, isopropyl, tert-butyl, fluoro-tert-butyl, difluoro-tert-butyl, or represents cyclopropyl, cyclopentyl or cyclohexyl, each of which is optionally monosubstituted to trisubstituted by identical or different substituents from the series consisting of fluorine, chlorine and/or methyl, or represents cycloalkyl having 3 to 6 carbon atoms in the cycloalkyl moiety and 1 or 2 carbon atoms in the alkyl moiety, phenyl which is optionally monosubstituted or disubstituted by identical or different substituents from the series consisting of fluorine, chlorine and/or bromine, or benzyl which is optionally monosubstituted or disubstituted by identical or different substituents from the series consisting of fluorine, chlorine and/or bromine, $X^4$ especially preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl or phenoxy, r also especially preferably represents the numbers 0, 1, 2 or 3, $X^4$ representing identical or different radicals if r represents 2 or 3 and $Y^2$ also especially represents an oxygen atom or a $CH_2$ group.

$R^1$ furthermore especially preferably represents a radical of the formula

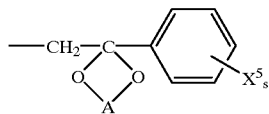

in which

A especially preferably represents alkanediyl having 2 or 3 carbon atoms which is optionally monosubstituted to trisubstituted by identical or different substituents from the series consisting of fluorine, chlorine, bromine, methyl, ethyl, n-propyl, isopropyl, n-butyl, i-butyl, sec-butyl, and/or tert-butyl, $X^5$ especially preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally monosubstituted to trisubstituted by identical or different substituents from the series consisting of fluorine, chlorine and/or methyl, and/or phenoxy which is optionally monosubstituted to trisubstituted by identical or different substituents from the series consisting of fluorine, chlorine and/or methyl and s also especially preferably represents the numbers 0, 1, 2 or 3, $X^5$ representing identical or different radicals if s represents 2 or 3.

$R^1$ furthermore preferably represents a radical of the formula

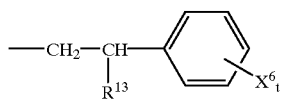

in which $R^{13}$ especially preferably represents methyl, ethyl, n-propyl, isopropyl, n-butyl, isobutyl, sec-butyl, tert-butyl, halogenoalkyl having 1 to 4 carbon atoms and 1 to 5 fluorine, chlorine and/or bromine atoms, fluoroalkoxyalkyl having 1 or 2 carbon atoms and 1 to 5 fluorine atoms in the fluoroalkoxy moiety and 1 or 2 carbon atoms in the alkyl moiety, or represents cyclopropyl, cyclopentyl or cyclohexyl, each of which is optionally monosubstituted to trisubstituted by identical or different substituents from the series consisting of fluorine, chlorine and/or methyl, or represents cycloalkylalkyl having 3 to 6 carbon atoms in the cycloalkyl moiety and 1 or 2 carbon atoms in the alkyl moiety, or represents phenyl which is optionally monosubstituted or disubtituted by identical or different substituents from the series consisting of fluorine, chlorine and/or bromine, or represents benzyl which is optionally monosubstituted or disubstituted by identical or different substituents from the series consisting of fluorine, chlorine and/or bromine, $X^6$ especially preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy and t also especially preferably represents the numbers 0, 1, 2 or 3, $X^6$ representing identical or different radicals if t represents 2 or 3.

$R^1$ furthermore especially preferably represents a radical of the formula

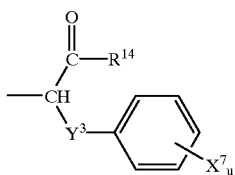

in which $R^{14}$ especially preferably represents methyl, isopropyl, tert-butyl, fluoro-tert-butyl, difluoro-tert-butyl, or represents cyclopropyl, cyclopentyl or cyclohexyl, each of which is optionally monosubstituted to trisubstituted by identical or different substituents from the series consisting of fluorine, chlorine and/or methyl, or represents cycloalkylalkyl having 3 to 6 carbon atoms in the cycloalkyl moiety and 1 or 2 carbon atoms in the alkyl moiety, phenyl which is optionally monosubstituted or disubstituted by identical or different substituents from the series consisting of fluorine, chlorine and/or bromine, or benzyl which is optionally monosubstituted or disubstituted by identical or different substituents from the series consisting of fluorine, chlorine and/or bromine, $X^7$ especially preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, $Y^3$ also especially preferably represents an oxygen atom or a $CH_2$ group, and u also especially preferably represents the numbers 0, 1, 2 or 3, $X^7$ representing identical or different radicals if u represents 2 or 3.

Moreover, $R^1$ also preferably represents a radical of the formula

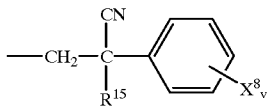

in which $R^{15}$ especially preferably represents methyl, ethyl, n-propyl, isopropyl, n-butyl, sec-butyl, isobutyl, tert-butyl, fluoro-tert-butyl, difluoro-tert-butyl, phenyl which is optionally monosubstituted or disubstituted by identical or different substituents from the series consisting of fluorine, chlorine, methyl, ethyl, trifluoromethyl, trichloromethyl, methoxy, ethoxy, trifluoromethoxy and/or difluoromethoxy, or represents phenylalkyl having 1 or 2 carbon atoms in the alkyl moiety which is optionally monosubstituted or disubstituted in the phenyl moiety by identical or different substituents from the series consisting of fluorine, chlorine, bromine, methyl, ethyl, trifluomethyl, trichloromethyl, methoxy, ethoxy, trifluoromethoxy and/or difluoromethoxy, $X^8$ especially preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, and v also especially preferably represents the numbers 0, 1, 2 or 3, $X^8$ representing identical or different radicals if v represents 2 or 3.

Other preferred compounds according to the invention are adducts of acids and those mercapto-imidazolyl derivatives of the formula (I) in which R and $R^1$ have those meanings which have been mentioned as being especially preferred for these substituents.

The acids which can be subjected to the addition reaction preferably include hydrohalic acids such as, for example hydrochloric acid and hydrobromic acid, in particular hydrochloric acid, furthermore phosphoric acid, nitric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid and 1,5-naphthalenedisulphonic acid, and also saccharin and thiosaccharin.

Other preferred compounds according to the invention are adducts of salts of metals of main groups II to IV and sub-groups I and II and IV to VIII of the Periodic Table and those mercapto-imidazolyl derivatives of the formula (I) in which R and $R^1$ have those meanings which have been mentioned as being preferred for these substituents.

Salts of copper, zinc, manganese, magnesium, tin, iron and of nickel are especially preferred in this context. Suitable anions of these salts are those which are derived from those acids which lead to physiologically acceptable adducts. Especially preferred acids of this type are, in this context, the hydrohalic acids such as, for example, hydrochloric acid and hydrobromic acid, furthermore phosphoric acid, nitric acid and sulphuric acid.

The mercapto-imidazolyl derivatives of the formula (I) according to the invention in which R represents hydrogen can exist in the "mercapto" form, of the formula

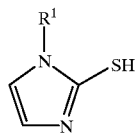

(Ia)

or in the tautomeric "thiono" form, of the formula

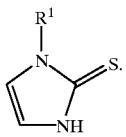

(Ib)

For the sake of simplicity, only the "mercapto" form is shown in each case.

Examples of substances according to the invention which may be mentioned are the mercapto-imidazolyl derivatives shown in the tables which follow.

TABLE 1

(Ic)

| $R^2$ | $R^3$ | R |
|---|---|---|
| Cl—⌬—CH$_2$—CH$_2$— | —C(CH$_3$)$_3$ | —CH$_3$ |
| Cl—⌬—CH$_2$—CH$_2$— | —C(CH$_3$)$_3$ | H |
| Cl—⌬—CH$_2$— | —C(CH$_3$)$_3$ | —CH$_3$ |
| Cl—⌬—CH$_2$— | —C(CH$_3$)$_3$ | H |
| Cl—⌬—CH(CH$_3$)— | —C(CH$_3$)$_3$ | —CH$_3$ |
| Cl—⌬—CH(CH$_3$)— | —C(CH$_3$)$_3$ | H |
| F—⌬— | F—⌬— | —CH$_3$ |

TABLE 1-continued (Ic)

Structure: 2-(1H-imidazol-1-yl)-1-R²-1-R³-ethanol with 2-S-R substituent on imidazole

| R² | R³ | R |
|---|---|---|
| 4-F-C₆H₄— | 2-F-C₆H₄— | H |
| 2,4-Cl₂-C₆H₃— | —C₄H₉-n | —CH₃ |
| 2,4-Cl₂-C₆H₃— | —C₄H₉-n | H |
| 4-Cl-C₆H₄— | —CH(CH₃)-cyclopropyl | —CH₃ |
| 4-Cl-C₆H₄— | —CH(CH₃)-cyclopropyl | H |
| 4-Cl-C₆H₄—O—CH₂— | —C(CH₃)₃ | —CH₃ |
| 4-Cl-C₆H₄—O—CH₂— | —C(CH₃)₃ | H |
| Cl₂CH—CCl₂—CH₂— | —C(CH₃)₃ | —CH₃ |
| Cl₂CH—CCl₂—CH₂— | —C(CH₃)₃ | H |
| Cl₂CH—CCl₂—CH₂— | cyclopropyl-Cl | —CH₃ |
| Cl₂CH—CCl₂—CH₂— | cyclopropyl-Cl | H |
| Cl₂CH—CCl₂—CH₂— | cyclopropyl-F | —CH₃ |
| Cl₂CH—CCl₂—CH₂— | cyclopropyl-F | H |
| 4-Cl-C₆H₄—CH=CH— | —C(CH₃)₃ | —CH₃ |
| 4-Cl-C₆H₄—CH=CH— | —C(CH₃)₃ | H |
| 4-Cl-C₆H₄—CH=CH— | cyclopropyl-Cl | —CH₃ |
| 4-Cl-C₆H₄—CH₂—CH₂— | cyclopropyl-Cl | H |
| 4-Cl-C₆H₄—CH₂— | cyclopropyl-Cl | H |
| 4-Cl-C₆H₄—CH(CH₃)— | cyclopropyl-Cl | H |
| 4-Cl-C₆H₄—O—CH₂— | cyclopropyl-Cl | —CH₃ |
| Cl₂CH—CCl₂— | cyclopropyl-Cl | —CH₃ |
| 2-furyl-CH₂—CH₂— | —C(CH₃)₃ | —CH₃ |
| 2-pyridyl-CH₂—CH₂— | —C(CH₃)₃ | —CH₃ |
| Cl₂C=CCl—CH₂— | cyclopropyl-Cl | H |
| Cl₂C=CCl—CH₂— | cyclopropyl-Cl | CH₃ |

TABLE 2

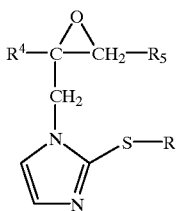

(Id)

| R⁴ | R⁵ | R |
|---|---|---|
| phenyl | 2-Cl-phenyl | —CH₃ |
| 4-Cl-phenyl | 2-Cl-phenyl | —CH₃ |
| 4-biphenyl | 2-Cl-phenyl | —CH₃ |
| 2,4-diCl-phenyl | 2-Cl-phenyl | —CH₃ |
| 2-Cl-phenyl | 2-Cl-phenyl | —CH₃ |
| 2-F-phenyl | 2-Cl-phenyl | —CH₃ |
| 4-CH₃-phenyl | 2-Cl-phenyl | —CH₃ |
| —C(CH₃)₂CH₂F | 2-Cl-phenyl | —CH₃ |

TABLE 2-continued

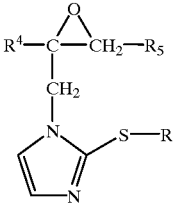

(Id)

| R⁴ | R⁵ | R |
|---|---|---|
| 3-Br-4-F-phenyl | 2-Cl-phenyl | —CH₃ |
| 4-Br-phenyl | 2-Cl-phenyl | —CH₃ |
| 3,4-diCl-phenyl | 2-Cl-phenyl | —CH₃ |
| 4-C(CH₃)₃-phenyl | 2-Cl-phenyl | —CH₃ |
| 3-Cl-phenyl | 2-Cl-phenyl | —CH₃ |
| 3,5-diCl-phenyl | 2-Cl-phenyl | —CH₃ |
| 4-phenoxy-phenyl | 2-Cl-phenyl | —CH₃ |
| 4-OCF₃-phenyl | 2-Cl-phenyl | —CH₃ |

TABLE 2-continued (Id)

$$R^4 - \underset{CH_2}{\overset{O}{C}} - CH_2 - R_5$$

(imidazole with N-CH2 linker and 2-S-R substituent)

| R⁴ | R⁵ | R |
|---|---|---|
| 4-(SCF₃)-C₆H₄- | 2-Cl-C₆H₄- | —CH₃ |
| 4-F-C₆H₄- | 2-(OCHF₂)-C₆H₄- | —CH₃ |
| 4-Cl-C₆H₄- | 2-F-C₆H₄- | —CH₃ |
| 4-biphenyl- | 2-F-C₆H₄- | —CH₃ |
| C₆H₅- | 2-F-C₆H₄- | —CH₃ |
| 2,4-Cl₂-C₆H₃- | 2-F-C₆H₄- | —CH₃ |
| 2-Cl-C₆H₄- | 2-F-C₆H₄- | —CH₃ |
| 3-F-C₆H₄- | 2-F-C₆H₄- | —CH₃ |
| 4-CH₃-C₆H₄- | 2-F-C₆H₄- | —CH₃ |
| 4-F-C₆H₄- | 2-F-C₆H₄- | —CH₃ |
| 3-Br-4-F-C₆H₃- | 2-F-C₆H₄- | —CH₃ |
| 4-Br-C₆H₄- | 2-F-C₆H₄- | —CH₃ |
| 3,4-Cl₂-C₆H₃- | 2-F-C₆H₄- | —CH₃ |
| 4-C(CH₃)₃-C₆H₄- | 2-F-C₆H₄- | —CH₃ |
| 3-Cl-C₆H₄- | 2-F-C₆H₄- | —CH₃ |
| 3,5-Cl₂-C₆H₃- | 2-F-C₆H₄- | —CH₃ |

TABLE 2-continued (Id)

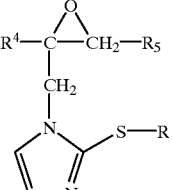

| R⁴ | R⁵ | R |
|---|---|---|
| 4-phenoxyphenyl | 2-F-phenyl | —CH₃ |
| 4-Cl-phenyl | 2-Br-phenyl | —CH₃ |
| phenyl | 2-Br-phenyl | —CH₃ |
| 4-biphenyl | 2-Br-phenyl | —CH₃ |
| 2,4-diCl-phenyl | 2-Br-phenyl | —CH₃ |
| 2-Cl-phenyl | 2-Br-phenyl | —CH₃ |
| 2-F-phenyl | 2-Br-phenyl | —CH₃ |
| 4-CH₃-phenyl | 2-Br-phenyl | —CH₃ |
| 4-F-phenyl | 2-Br-phenyl | —CH₃ |
| 3-Br-4-F-phenyl | 2-Br-phenyl | —CH₃ |
| 4-Br-phenyl | 2-Br-phenyl | —CH₃ |
| 3,4-diCl-phenyl | 2-Br-phenyl | —CH₃ |
| 4-C(CH₃)₃-phenyl | 2-Br-phenyl | —CH₃ |
| 3-Cl-phenyl | 2-Br-phenyl | —CH₃ |
| 3,5-diCl-phenyl | 2-Br-phenyl | —CH₃ |
| 4-phenoxyphenyl | 2-Br-phenyl | —CH₃ |

TABLE 2-continued
(Id)
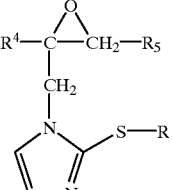
| R⁴ | R⁵ | R |
|---|---|---|
| —CH₃ | 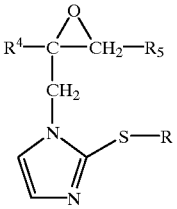 | —CH₃ |
| —CH₃ | 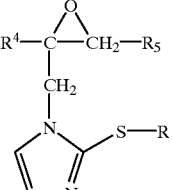 | —CH₃ |
| —CH₃ | 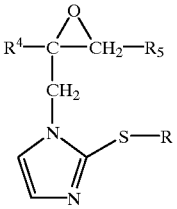 | —CH₃ |
| —C(CH₃)₃ | 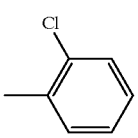 | —CH₃ |
| 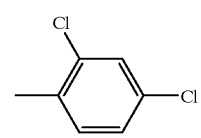 | 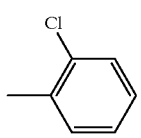 | —CH₃ |
| 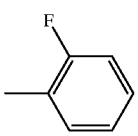 | 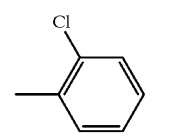 | H |
| 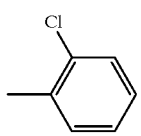 | 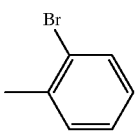 | H |
| 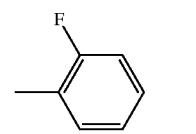 | 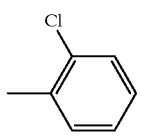 | H |
TABLE 2-continued
(Id)
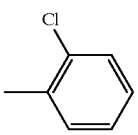
| R⁴ | R⁵ | R |
|---|---|---|
| 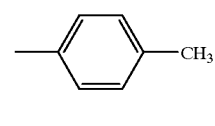 | 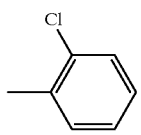 | H |
|  | 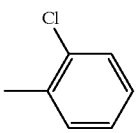 | H |
| 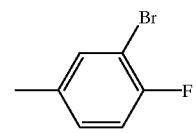 | 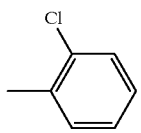 | H |
| 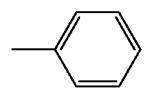 | 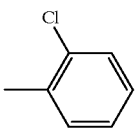 | H |
| 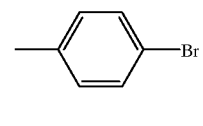 | 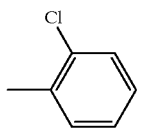 | H |
| 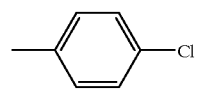 | 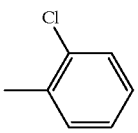 | H |
| 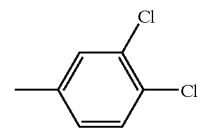 | 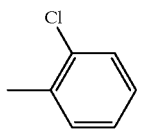 | H |
| 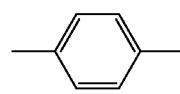 | 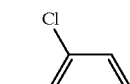 | H |

TABLE 2-continued (Id)

$$R^4-\underset{\underset{\underset{N}{\overset{|}{\underset{\parallel}{\bigvee}}}}{\overset{|}{\underset{CH_2}{\bigvee}}}}{\overset{O}{\overset{\diagup\diagdown}{C}}}-CH_2-R_5$$

| R⁴ | R⁵ | R |
|---|---|---|
| 4-tBu-C₆H₄- | 2-Cl-C₆H₄- | H |
| 3-Cl-C₆H₄- | 2-Cl-C₆H₄- | H |
| 3,5-diCl-C₆H₃- | 2-Cl-C₆H₄- | H |
| 4-PhO-C₆H₄- | 2-Cl-C₆H₄- | H |
| 4-OCF₃-C₆H₄- | 2-Cl-C₆H₄- | H |
| 4-SCF₃-C₆H₄- | 2-Cl-C₆H₄- | H |
| 4-F-C₆H₄- | 2-OCHF₂-C₆H₄- | H |
| 4-Cl-C₆H₄- | 2-F-C₆H₄- | H |
| 4-Ph-C₆H₄- | 2-F-C₆H₄- | H |
| C₆H₅- | 2-F-C₆H₄- | H |
| 2,4-diCl-C₆H₃- | 2-F-C₆H₄- | H |
| 3-Cl-C₆H₄- | 2-F-C₆H₄- | H |
| 2-F-C₆H₄- | 2-F-C₆H₄- | H |
| 4-CH₃-C₆H₄- | 2-F-C₆H₄- | H |
| 4-F-C₆H₄- | 2-F-C₆H₄- | H |
| 2-Br-4-F-C₆H₃- | 2-F-C₆H₄- | H |

TABLE 2-continued (Id)

$$\text{R}^4-\overset{\overset{\displaystyle O}{\diagup\diagdown}}{C}-CH_2-R_5$$
$$\overset{|}{CH_2}$$
attached to N of imidazole with 2-S-R

| R⁴ | R⁵ | R |
|---|---|---|
| 4-Br-phenyl | 2-F-phenyl | H |
| 3,4-diCl-phenyl | 2-F-phenyl | H |
| 4-C(CH₃)₃-phenyl | 2-F-phenyl | H |
| 3-Cl-phenyl | 2-F-phenyl | H |
| 3,5-diCl-phenyl | 2-F-phenyl | H |
| 4-phenoxy-phenyl | 2-F-phenyl | H |
| 4-Cl-phenyl | 2-Br-phenyl | H |
| phenyl | 2-Br-phenyl | H |
| 4-biphenyl | 2-Br-phenyl | H |
| 2,4-diCl-phenyl | 2-Br-phenyl | H |
| 2-Cl-phenyl | 2-Br-phenyl | H |
| 3-F-phenyl | 2-Br-phenyl | H |
| 4-CH₃-phenyl | 2-Br-phenyl | H |
| 4-F-phenyl | 2-Br-phenyl | H |
| 3-Br-4-F-phenyl | 2-Br-phenyl | H |
| 3-Br-phenyl | 2-Br-phenyl | H |

TABLE 2-continued (Id) Structure: R4-C(epoxide-CH2-R5)-CH2-N(imidazole with 2-S-R)

| R4 | R5 | R |
|---|---|---|
| 3,4-dichlorophenyl | 2-bromophenyl | H |
| 4-tert-butylphenyl | 2-bromophenyl | H |
| 3-chlorophenyl | 2-bromophenyl | H |
| -C(CH3)2-CH2F (neopentyl-F) | 2-chlorophenyl | H |
| 3,5-dichlorophenyl | 2-bromophenyl | H |
| 4-phenoxyphenyl | 2-bromophenyl | H |
| —CH3 | 2-chlorophenyl | H |
| —CH3 | 2,4-dichlorophenyl | H |
| —CH3 | 2-bromophenyl | H |
| —C(CH3)3 | 2-chlorophenyl | H |
| 1-chlorocyclopropyl | 2-chlorophenyl | H |

TABLE 3

(Ie) Structure: cyclopentane with R6, R7 on one carbon, adjacent carbon bearing OH and CH2-N(imidazole-2-S-R), and next carbon bearing CH2-phenyl(X1m)

| R6 | R7 | R | X1m |
|---|---|---|---|
| —CH3 | —CH3 | —CH3 | 4-Br |
| —CH3 | —CH3 | —CH3 | 4-F |
| —CH3 | —CH3 | —CH3 | 2,4-Cl2 |
| —CH3 | H | —CH3 | 4-Cl |
| —CH3 | —CH3 | —CH3 | — |
| —CH3 | —CH3 | —CH3 | 4-CH3 |
| —CH3 | —CH3 | —CH3 | 2-F, 4-Cl |
| —C2H5 | H | —CH3 | 4-Cl |
| —C2H5 | —C2H5 | —CH3 | 4-Cl |
| —C3H7-n | H | —CH3 | 4-Cl |
| —C2H5 | H | —CH3 | 2,4-Cl2 |
| —C2H5 | H | —CH3 | 4-F |
| —C2H5 | H | —CH3 | 4-Br |
| —C2H5 | H | —CH3 | 4-phenyl |
| —C2H5 | H | —CH3 | 4-C4H9-t |
| —C3H7-i | H | —CH3 | 4-Cl |
| —C5H11-n | H | —CH3 | 4-Cl |

TABLE 3-continued (Ie)

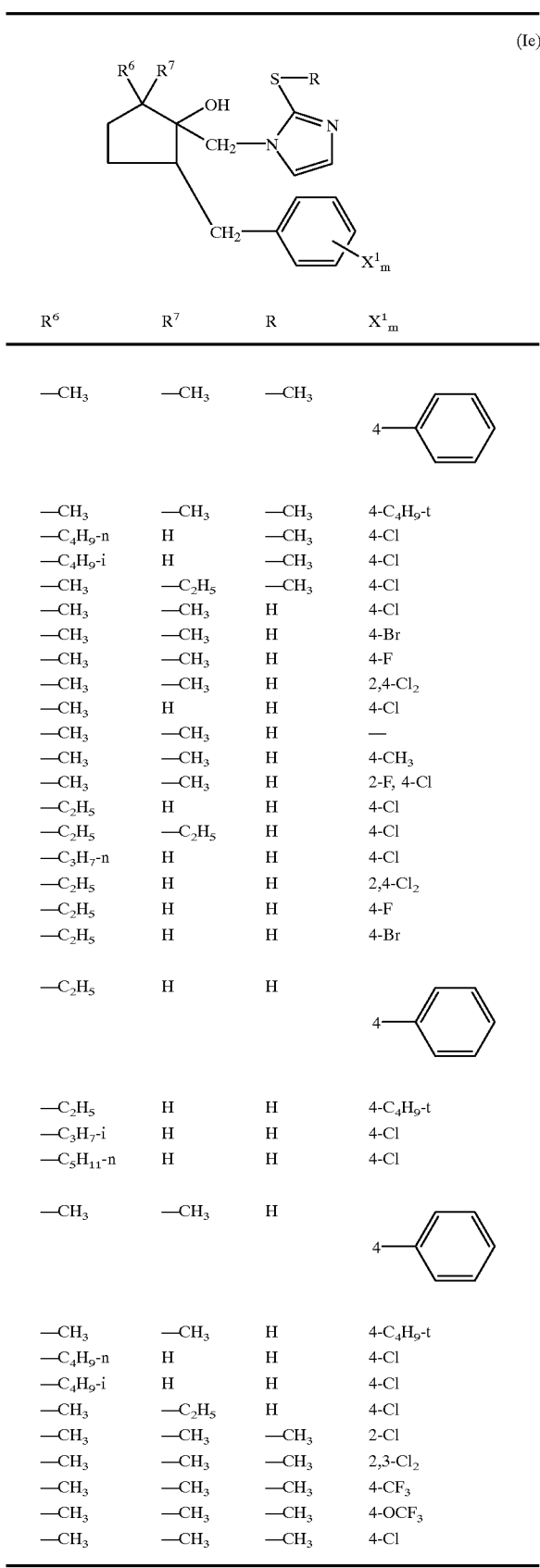

| R[6] | R[7] | R | $X^1_m$ |
|---|---|---|---|
| —CH₃ | —CH₃ | —CH₃ | 4-phenyl |
| —CH₃ | —CH₃ | —CH₃ | 4-C₄H₉-t |
| —C₄H₉-n | H | —CH₃ | 4-Cl |
| —C₄H₉-i | H | —CH₃ | 4-Cl |
| —CH₃ | —C₂H₅ | —CH₃ | 4-Cl |
| —CH₃ | —CH₃ | H | 4-Cl |
| —CH₃ | —CH₃ | H | 4-Br |
| —CH₃ | —CH₃ | H | 4-F |
| —CH₃ | —CH₃ | H | 2,4-Cl₂ |
| —CH₃ | H | H | 4-Cl |
| —CH₃ | —CH₃ | H | — |
| —CH₃ | —CH₃ | H | 4-CH₃ |
| —CH₃ | —CH₃ | H | 2-F, 4-Cl |
| —C₂H₅ | H | H | 4-Cl |
| —C₂H₅ | —C₂H₅ | H | 4-Cl |
| —C₃H₇-n | H | H | 4-Cl |
| —C₂H₅ | H | H | 2,4-Cl₂ |
| —C₂H₅ | H | H | 4-F |
| —C₂H₅ | H | H | 4-Br |
| —C₂H₅ | H | H | 4-phenyl |
| —C₂H₅ | H | H | 4-C₄H₉-t |
| —C₃H₇-i | H | H | 4-Cl |
| —C₅H₁₁-n | H | H | 4-Cl |
| —CH₃ | —CH₃ | H | 4-phenyl |
| —CH₃ | —CH₃ | H | 4-C₄H₉-t |
| —C₄H₉-n | H | H | 4-Cl |
| —C₄H₉-i | H | H | 4-Cl |
| —CH₃ | —C₂H₅ | H | 4-Cl |
| —CH₃ | —CH₃ | —CH₃ | 2-Cl |
| —CH₃ | —CH₃ | —CH₃ | 2,3-Cl₂ |
| —CH₃ | —CH₃ | —CH₃ | 4-CF₃ |
| —CH₃ | —CH₃ | —CH₃ | 4-OCF₃ |
| —CH₃ | —CH₃ | —CH₃ | 4-Cl |

TABLE 4

(If)

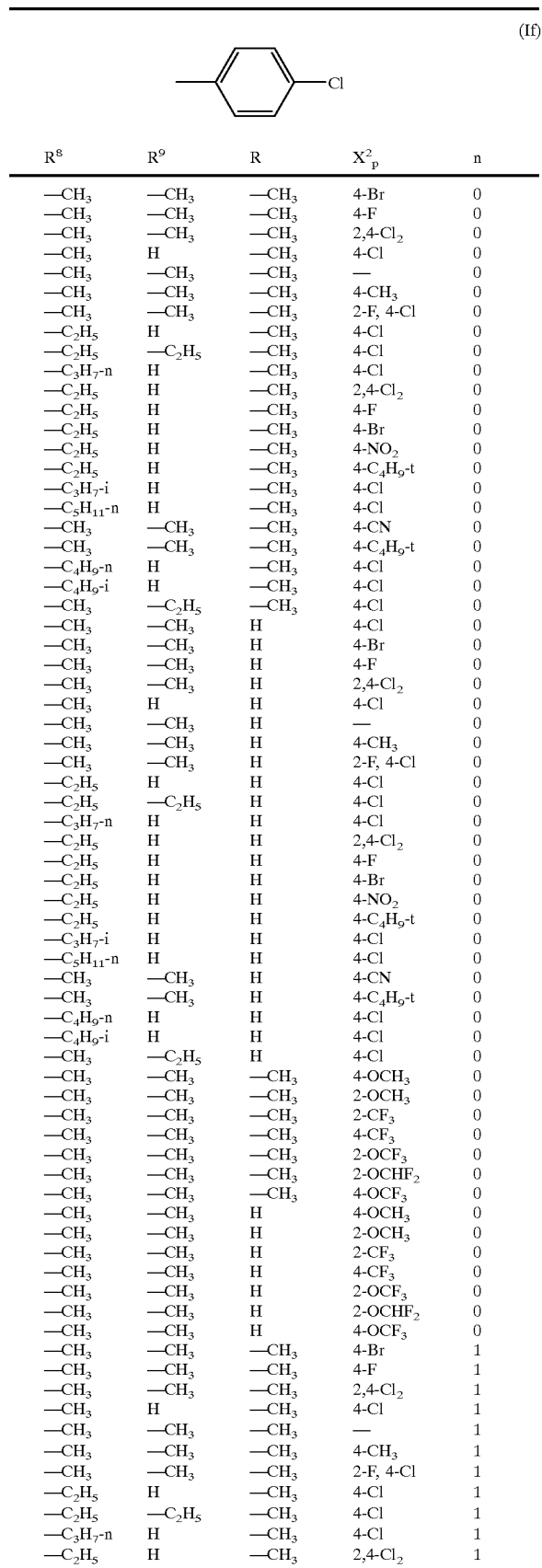

| R[8] | R[9] | R | $X^2_p$ | n |
|---|---|---|---|---|
| —CH₃ | —CH₃ | —CH₃ | 4-Br | 0 |
| —CH₃ | —CH₃ | —CH₃ | 4-F | 0 |
| —CH₃ | —CH₃ | —CH₃ | 2,4-Cl₂ | 0 |
| —CH₃ | H | —CH₃ | 4-Cl | 0 |
| —CH₃ | —CH₃ | —CH₃ | — | 0 |
| —CH₃ | —CH₃ | —CH₃ | 4-CH₃ | 0 |
| —CH₃ | —CH₃ | —CH₃ | 2-F, 4-Cl | 0 |
| —C₂H₅ | H | —CH₃ | 4-Cl | 0 |
| —C₂H₅ | —C₂H₅ | —CH₃ | 4-Cl | 0 |
| —C₃H₇-n | H | —CH₃ | 4-Cl | 0 |
| —C₂H₅ | H | —CH₃ | 2,4-Cl₂ | 0 |
| —C₂H₅ | H | —CH₃ | 4-F | 0 |
| —C₂H₅ | H | —CH₃ | 4-Br | 0 |
| —C₂H₅ | H | —CH₃ | 4-NO₂ | 0 |
| —C₂H₅ | H | —CH₃ | 4-C₄H₉-t | 0 |
| —C₃H₇-i | H | —CH₃ | 4-Cl | 0 |
| —C₅H₁₁-n | H | —CH₃ | 4-Cl | 0 |
| —CH₃ | —CH₃ | —CH₃ | 4-CN | 0 |
| —CH₃ | —CH₃ | —CH₃ | 4-C₄H₉-t | 0 |
| —C₄H₉-n | H | —CH₃ | 4-Cl | 0 |
| —C₄H₉-i | H | —CH₃ | 4-Cl | 0 |
| —CH₃ | —C₂H₅ | —CH₃ | 4-Cl | 0 |
| —CH₃ | —CH₃ | H | 4-Cl | 0 |
| —CH₃ | —CH₃ | H | 4-Br | 0 |
| —CH₃ | —CH₃ | H | 4-F | 0 |
| —CH₃ | —CH₃ | H | 2,4-Cl₂ | 0 |
| —CH₃ | H | H | 4-Cl | 0 |
| —CH₃ | —CH₃ | H | — | 0 |
| —CH₃ | —CH₃ | H | 4-CH₃ | 0 |
| —CH₃ | —CH₃ | H | 2-F, 4-Cl | 0 |
| —C₂H₅ | H | H | 4-Cl | 0 |
| —C₂H₅ | —C₂H₅ | H | 4-Cl | 0 |
| —C₃H₇-n | H | H | 4-Cl | 0 |
| —C₂H₅ | H | H | 2,4-Cl₂ | 0 |
| —C₂H₅ | H | H | 4-F | 0 |
| —C₂H₅ | H | H | 4-Br | 0 |
| —C₂H₅ | H | H | 4-NO₂ | 0 |
| —C₂H₅ | H | H | 4-C₄H₉-t | 0 |
| —C₃H₇-i | H | H | 4-Cl | 0 |
| —C₅H₁₁-n | H | H | 4-Cl | 0 |
| —CH₃ | —CH₃ | H | 4-CN | 0 |
| —CH₃ | —CH₃ | H | 4-C₄H₉-t | 0 |
| —C₄H₉-n | H | H | 4-Cl | 0 |
| —C₄H₉-i | H | H | 4-Cl | 0 |
| —CH₃ | —C₂H₅ | H | 4-Cl | 0 |
| —CH₃ | —CH₃ | —CH₃ | 4-OCH₃ | 0 |
| —CH₃ | —CH₃ | —CH₃ | 2-OCH₃ | 0 |
| —CH₃ | —CH₃ | —CH₃ | 2-CF₃ | 0 |
| —CH₃ | —CH₃ | —CH₃ | 4-CF₃ | 0 |
| —CH₃ | —CH₃ | —CH₃ | 2-OCF₃ | 0 |
| —CH₃ | —CH₃ | —CH₃ | 2-OCHF₂ | 0 |
| —CH₃ | —CH₃ | —CH₃ | 4-OCF₃ | 0 |
| —CH₃ | —CH₃ | H | 4-OCH₃ | 0 |
| —CH₃ | —CH₃ | H | 2-OCH₃ | 0 |
| —CH₃ | —CH₃ | H | 2-CF₃ | 0 |
| —CH₃ | —CH₃ | H | 4-CF₃ | 0 |
| —CH₃ | —CH₃ | H | 2-OCF₃ | 0 |
| —CH₃ | —CH₃ | H | 2-OCHF₂ | 0 |
| —CH₃ | —CH₃ | H | 4-OCF₃ | 0 |
| —CH₃ | —CH₃ | —CH₃ | 4-Br | 1 |
| —CH₃ | —CH₃ | —CH₃ | 4-F | 1 |
| —CH₃ | —CH₃ | —CH₃ | 2,4-Cl₂ | 1 |
| —CH₃ | H | —CH₃ | 4-Cl | 1 |
| —CH₃ | —CH₃ | —CH₃ | — | 1 |
| —CH₃ | —CH₃ | —CH₃ | 4-CH₃ | 1 |
| —CH₃ | —CH₃ | —CH₃ | 2-F, 4-Cl | 1 |
| —C₂H₅ | H | —CH₃ | 4-Cl | 1 |
| —C₂H₅ | —C₂H₅ | —CH₃ | 4-Cl | 1 |
| —C₃H₇-n | H | —CH₃ | 4-Cl | 1 |
| —C₂H₅ | H | —CH₃ | 2,4-Cl₂ | 1 |

TABLE 4-continued (If)

Structure: 4-chlorophenyl group

| R⁸ | R⁹ | R | X²ₚ | n |
|---|---|---|---|---|
| —C₂H₅ | H | —CH₃ | 4-F | 1 |
| —C₂H₅ | H | —CH₃ | 4-Br | 1 |
| —C₂H₅ | H | —CH₃ | 4-NO₂ | 1 |
| —C₂H₅ | H | —CH₃ | 4-C₄H₉-t | 1 |
| —C₃H₇-i | H | —CH₃ | 4-Cl | 1 |
| —C₅H₁₁-n | H | —CH₃ | 4-Cl | 1 |
| —CH₃ | —CH₃ | —CH₃ | 4-CN | 1 |
| —CH₃ | —CH₃ | —CH₃ | 4-C₄H₉-t | 1 |
| —C₄H₉-n | H | —CH₃ | 4-Cl | 1 |
| —CH₃ | —CH₃ | —CH₃ | 4-Cl | 1 |
| —CH₃ | —CH₃ | H | 4-Cl | 1 |
| —C₄H₉-i | H | —CH₃ | 4-Cl | 1 |
| —CH₃ | —C₂H₅ | —CH₃ | 4-Cl | 1 |
| —CH₃ | —CH₃ | H | 4-Cl | 1 |
| —CH₃ | —CH₃ | H | 4-Br | 1 |
| —CH₃ | —CH₃ | H | 4-F | 1 |
| —CH₃ | —CH₃ | H | 2,4-Cl₂ | 1 |
| —CH₃ | H | H | 4-Cl | 1 |
| —CH₃ | —CH₃ | H | — | 1 |
| —CH₃ | —CH₃ | H | 4-CH₃ | 1 |
| —CH₃ | —CH₃ | H | 2-F, 4-Cl | 1 |
| —C₂H₅ | H | H | 4-Cl | 1 |
| —C₂H₅ | —C₂H₅ | H | 4-Cl | 1 |
| —C₃H₇-n | H | H | 4-Cl | 1 |
| —C₂H₅ | H | H | 2,4-Cl₂ | 1 |
| —C₂H₅ | H | H | 4-F | 1 |
| —C₂H₅ | H | H | 4-Br | 1 |
| —C₂H₅ | H | H | 4-NO₂ | 1 |
| —C₂H₅ | H | H | 4-C₄H₉-t | 1 |
| —C₃H₇-i | H | H | 4-Cl | 1 |
| —C₅H₁₁-n | H | H | 4-Cl | 1 |
| —CH₃ | —CH₃ | H | 4-CN | 1 |
| —CH₃ | —CH₃ | H | 4-C₄H₉-t | 1 |
| —C₄H₉-n | H | H | 4-Cl | 1 |
| —C₄H₉-i | H | H | 4-Cl | 1 |
| —CH₃ | —C₂H₅ | H | 4-Cl | 1 |
| —CH₃ | —CH₃ | —CH₃ | 4-OCH₃ | 1 |
| —CH₃ | —CH₃ | —CH₃ | 2-OCH₃ | 1 |
| —CH₃ | —CH₃ | —CH₃ | 2-CF₃ | 1 |
| —CH₃ | —CH₃ | —CH₃ | 4-CF₃ | 1 |
| —CH₃ | —CH₃ | —CH₃ | 2-OCF₃ | 1 |
| —CH₃ | —CH₃ | —CH₃ | 2-OCHF₂ | 1 |
| —CH₃ | —CH₃ | —CH₃ | 4-OCF₃ | 1 |
| —CH₃ | —CH₃ | H | 4-OCH₃ | 1 |
| —CH₃ | —CH₃ | H | 2-OCH₃ | 1 |
| —CH₃ | —CH₃ | H | 2-CF₃ | 1 |
| —CH₃ | —CH₃ | H | 4-CF₃ | 1 |
| —CH₃ | —CH₃ | H | 2-OCF₃ | 1 |
| —CH₃ | —CH₃ | H | 2-OCHF₂ | 1 |
| —CH₃ | —CH₃ | H | 4-OCF₃ | 1 |
| —CH₃ | —CH₃ | —CH₃ | 2-Cl | 0 |
| —CH₃ | —CH₃ | —CH₃ | 2,3-Cl₂ | 0 |
| —CH₃ | —CH₃ | —CH₃ | 2-Cl | 1 |
| —CH₃ | —CH₃ | —CH₃ | 4-Cl | 0 |

TABLE 5

(Ig)

| R¹⁰ | R |
|---|---|
| 4-chlorophenyl | —CH₃ |
| phenyl | —CH₃ |
| 4-fluorophenyl | —CH₃ |
| 2,4-dichlorophenyl | —CH₃ |
| 4-methylphenyl | —CH₃ |
| 4-biphenyl | —CH₃ |
| 4-methoxyphenyl | —CH₃ |
| 4-phenoxyphenyl | —CH₃ |
| 2-(trifluoromethyl)phenyl | —CH₃ |
| —C₄H₉-n | —CH₃ |
| —C(CH₃)₃ | —CH₃ |
| —CH(CH₃)₂ | —CH₃ |
| —C(CH₂Cl)(CH₃)(CH₂Cl) | —CH₃ |

TABLE 5-continued $$\text{(Ig)}$$

Structure: R¹⁰–C(OH)(CH₂–triazolyl)(CH₂–N-imidazolyl-2-S–R)

| R¹⁰ | R |
|---|---|
| –C(CH₂F)(CH₃)(CH₂F) | –CH₃ |
| –CH₂–CH(CH₃)₂ | –CH₃ |
| cyclopropyl | –CH₃ |
| cyclopentyl | –CH₃ |
| cyclohexyl | –CH₃ |
| cyclopropyl-CH₃ | –CH₃ |
| cyclopropyl-Cl | –CH₃ |
| cyclopropyl-F | –CH₃ |
| 1-methylcyclohexyl | –CH₃ |
| –CH₂–(4-Cl-phenyl) | –CH₃ |
| –(2-methyl-6-OCHF₂-phenyl) | –CH₃ |
| –CH₂–(2-Cl-phenyl) | –CH₃ |
| –CH₂–(2,6-diCl-phenyl) | –CH₃ |
| –CH₂–phenyl | –CH₃ |
| –CH₂–(4-OCH₃-phenyl) | –CH₃ |
| –CH(CH₃)–C₂H₅ | –CH₃ |
| –CH₂–(4-F-phenyl) | –CH₃ |
| –CH(CH₃)–phenyl | –CH₃ |
| –CH(CH₃)–(4-Cl-phenyl) | –CH₃ |
| –CH(CH₃)–(4-F-phenyl) | –CH₃ |
| –CH(CH₃)–(4-CF₃-phenyl) | –CH₃ |
| –CH(CH₃)–(4-OCH₃-phenyl) | –CH₃ |

TABLE 5-continued (Ig)

[Structure: R¹⁰—C(OH)(CH₂-1,2,4-triazol-1-yl)—CH₂—N(imidazole with 2-S—R substituent)]

| R¹⁰ | R |
|---|---|
| —CH(CH₃)—C₆H₄—OCF₃ (4-) | —CH₃ |
| 2,6-dichlorophenyl-CH₂— | —CH₃ |
| 4-(OCF₃)phenyl- | —CH₃ |
| 2,4,5-trichlorophenyl- | —CH₃ |
| 3,4-dichlorophenyl- | —CH₃ |
| 4-chlorophenyl- | H |
| phenyl- | H |
| 4-fluorophenyl- | H |
| 2,4-dichlorophenyl- | H |
| 4-methylphenyl- | H |
| 4-phenylphenyl- (biphenyl) | H |
| 4-methoxyphenyl- | H |
| 4-phenoxyphenyl- | H |
| 2-(CF₃)phenyl- | H |
| —C₄H₉-n | H |
| —C(CH₃)₃ | H |
| —CH(CH₃)₂ | H |
| —C(CH₂Cl)₂CH₃ with CH₂Cl | H |
| —C(CH₃)₂CH₂F with CH₃ | H |
| —CH₂—CH(CH₃)₂ | H |
| cyclopropyl | H |
| cyclopentyl | H |
| cyclohexyl | H |

TABLE 5-continued
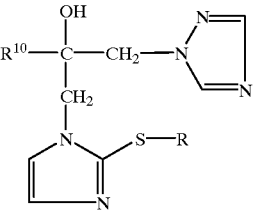
(Ig)
| R¹⁰ | R |
|---|---|
| 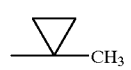 | H |
| 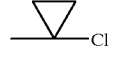 | H |
| 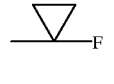 | H |
| 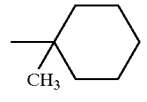 | H |
| 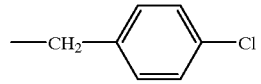 | H |
| 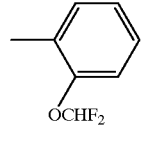 | H |
| 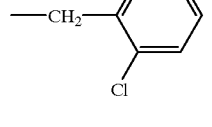 | H |
| 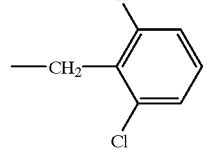 | H |
| 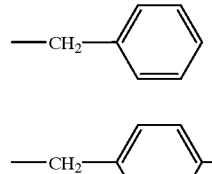 | H |
| 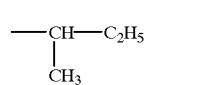 | H |
|  | H |
TABLE 5-continued
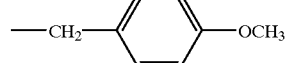
(Ig)
| R¹⁰ | R |
|---|---|
| 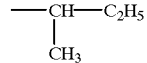 | H |
| 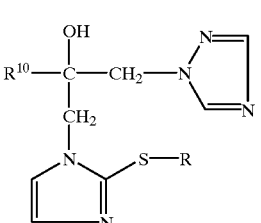 | H |
| 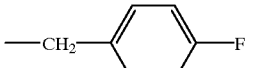 | H |
| 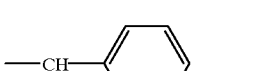 | H |
|  | H |
| 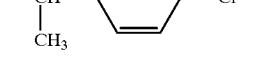 | H |
| 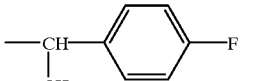 | H |
| 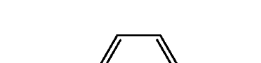 | H |
|  | H |

TABLE 5-continued

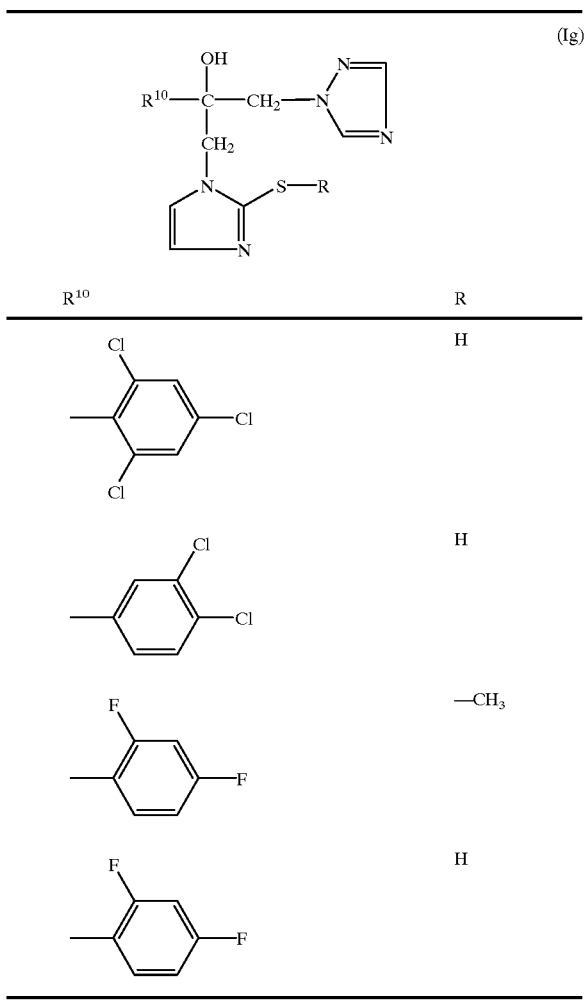

(Ig)

| R[10] | R |
|---|---|
| (2,4,5-trichlorophenyl) | H |
| (3,4-dichlorophenyl) | H |
| (2,4-difluorophenyl) | —CH$_3$ |
| (2,4-difluorophenyl) | H |

TABLE 6

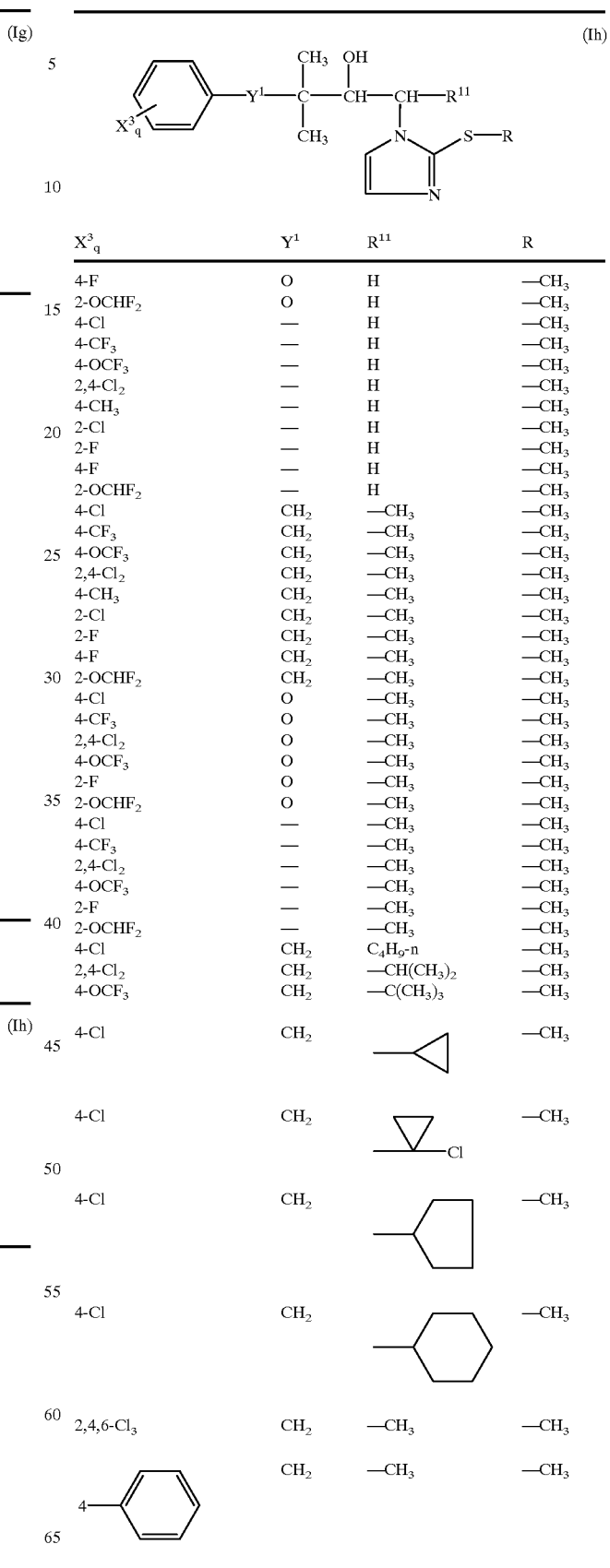

(Ih)

| X$^3_q$ | Y$^1$ | R$^{11}$ | R |
|---|---|---|---|
| 4-Cl | CH$_2$ | H | —CH$_3$ |
| 4-CF$_3$ | CH$_2$ | H | —CH$_3$ |
| 4-OCF$_3$ | CH$_2$ | H | —CH$_3$ |
| 2,4-Cl$_2$ | CH$_2$ | H | —CH$_3$ |
| 4-CH$_3$ | CH$_2$ | H | —CH$_3$ |
| 2-Cl | CH$_2$ | H | —CH$_3$ |
| 2-F | CH$_2$ | H | —CH$_3$ |
| 4-F | CH$_2$ | H | —CH$_3$ |
| 2-OCHF$_2$ | CH$_2$ | H | —CH$_3$ |
| 4-Cl | O | H | —CH$_3$ |
| 4-CF$_3$ | O | H | —CH$_3$ |
| 4-OCF$_3$ | O | H | —CH$_3$ |
| 2,4-Cl$_2$ | O | H | —CH$_3$ |
| 4-CH$_3$ | O | H | —CH$_3$ |
| 2-Cl | O | H | —CH$_3$ |
| 2-F | O | H | —CH$_3$ |
| 4-F | O | H | —CH$_3$ |
| 2-OCHF$_2$ | O | H | —CH$_3$ |
| 4-Cl | — | H | —CH$_3$ |
| 4-CF$_3$ | — | H | —CH$_3$ |
| 4-OCF$_3$ | — | H | —CH$_3$ |
| 2,4-Cl$_2$ | — | H | —CH$_3$ |
| 4-CH$_3$ | — | H | —CH$_3$ |
| 2-Cl | — | H | —CH$_3$ |
| 2-F | — | H | —CH$_3$ |
| 4-F | — | H | —CH$_3$ |
| 2-OCHF$_2$ | — | H | —CH$_3$ |
| 4-Cl | CH$_2$ | —CH$_3$ | —CH$_3$ |
| 4-CF$_3$ | CH$_2$ | —CH$_3$ | —CH$_3$ |
| 4-OCF$_3$ | CH$_2$ | —CH$_3$ | —CH$_3$ |
| 2,4-Cl$_2$ | CH$_2$ | —CH$_3$ | —CH$_3$ |
| 4-CH$_3$ | CH$_2$ | —CH$_3$ | —CH$_3$ |
| 2-Cl | CH$_2$ | —CH$_3$ | —CH$_3$ |
| 2-F | CH$_2$ | —CH$_3$ | —CH$_3$ |
| 4-F | CH$_2$ | —CH$_3$ | —CH$_3$ |
| 2-OCHF$_2$ | CH$_2$ | —CH$_3$ | —CH$_3$ |
| 4-Cl | O | —CH$_3$ | —CH$_3$ |
| 4-CF$_3$ | O | —CH$_3$ | —CH$_3$ |
| 2,4-Cl$_2$ | O | —CH$_3$ | —CH$_3$ |
| 4-OCF$_3$ | O | —CH$_3$ | —CH$_3$ |
| 2-F | O | —CH$_3$ | —CH$_3$ |
| 2-OCHF$_2$ | O | —CH$_3$ | —CH$_3$ |
| 4-Cl | — | —CH$_3$ | —CH$_3$ |
| 4-CF$_3$ | — | —CH$_3$ | —CH$_3$ |
| 2,4-Cl$_2$ | — | —CH$_3$ | —CH$_3$ |
| 4-OCF$_3$ | — | —CH$_3$ | —CH$_3$ |
| 2-F | — | —CH$_3$ | —CH$_3$ |
| 2-OCHF$_2$ | — | —CH$_3$ | —CH$_3$ |
| 4-Cl | CH$_2$ | C$_4$H$_9$-n | —CH$_3$ |
| 2,4-Cl$_2$ | CH$_2$ | —CH(CH$_3$)$_2$ | —CH$_3$ |
| 4-OCF$_3$ | CH$_2$ | —C(CH$_3$)$_3$ | —CH$_3$ |
| 4-Cl | CH$_2$ | cyclopropyl | —CH$_3$ |
| 4-Cl | CH$_2$ | chlorocyclopropyl | —CH$_3$ |
| 4-Cl | CH$_2$ | cyclopentyl | —CH$_3$ |
| 4-Cl | CH$_2$ | cyclohexyl | —CH$_3$ |
| 2,4,6-Cl$_3$ | CH$_2$ | —CH$_3$ | —CH$_3$ |
| 4-phenyl | CH$_2$ | —CH$_3$ | —CH$_3$ |

TABLE 6-continued (Ih)

| X$^3_q$ | Y$^1$ | R$^{11}$ | R |
|---|---|---|---|
| 4-F | O | H | —CH$_3$ |
| 2-OCHF$_2$ | O | H | —CH$_3$ |

TABLE 6-continued (Ih)

$$\text{X}^3_q\text{-C}_6\text{H}_4\text{-Y}^1\text{-C}(\text{CH}_3)_2\text{-CH(OH)-CH(R}^{11})\text{-N(imidazole-2-S-R)}$$

| $X^3_q$ | $Y^1$ | $R^{11}$ | R |
|---|---|---|---|
| 4-O-C$_6$H$_5$ | CH$_2$ | —CH$_3$ | —CH$_3$ |
| 4-Cl | CH$_2$ | H | H |
| 4-CF$_3$ | CH$_2$ | H | H |
| 4-OCF$_3$ | CH$_2$ | H | H |
| 2,4-Cl$_2$ | CH$_2$ | H | H |
| 4-CH$_3$ | CH$_2$ | H | H |
| 2-Cl | CH$_2$ | H | H |
| 2-F | CH$_2$ | H | H |
| 4-F | CH$_2$ | H | H |
| 2-OCHF$_2$ | CH$_2$ | H | H |
| 4-Cl | O | H | H |
| 4-CF$_3$ | O | H | H |
| 4-OCF$_3$ | O | H | H |
| 2,4-Cl$_2$ | O | H | H |
| 4-CH$_3$ | O | H | H |
| 2-Cl | O | H | H |
| 2-F | O | H | H |
| 4-F | O | H | H |
| 2-OCHF$_2$ | O | H | H |
| 4-Cl | — | H | H |
| 4-CF$_3$ | — | H | H |
| 4-OCF$_3$ | — | H | H |
| 2,4-Cl$_2$ | — | H | H |
| 4-CH$_3$ | — | H | H |
| 2-Cl | — | H | H |
| 2-F | — | H | H |
| 4-F | — | H | H |
| 2-OCHF$_2$ | — | H | H |
| 4-Cl | CH$_2$ | —CH$_3$ | H |
| 4-CF$_3$ | CH$_2$ | —CH$_3$ | H |
| 4-OCF$_3$ | CH$_2$ | —CH$_3$ | H |
| 2,4-Cl$_2$ | CH$_2$ | —CH$_3$ | H |
| 4-CH$_3$ | CH$_2$ | —CH$_3$ | H |
| 2-Cl | CH$_2$ | —CH$_3$ | H |
| 2-F | CH$_2$ | —CH$_3$ | H |
| 4-F | CH$_2$ | —CH$_3$ | H |
| 2-OCHF$_2$ | CH$_2$ | —CH$_3$ | H |
| 4-Cl | O | —CH$_3$ | H |
| 4-CF$_3$ | O | —CH$_3$ | H |
| 2,4-Cl$_2$ | O | —CH$_3$ | H |
| 4-OCF$_3$ | O | —CH$_3$ | H |
| 2-F | O | —CH$_3$ | H |
| 2-OCHF$_2$ | O | —CH$_3$ | H |
| 4-Cl | — | —CH$_3$ | H |
| 4-CF$_3$ | — | —CH$_3$ | H |
| 2,4-Cl$_2$ | — | —CH$_3$ | H |
| 4-OCF$_3$ | — | —CH$_3$ | H |
| 2-F | — | —CH$_3$ | H |
| 2-OCHF$_2$ | — | —CH$_3$ | H |
| 4-Cl | CH$_2$ | —C$_4$H$_9$-n | H |
| 2,4-Cl$_2$ | CH$_2$ | —CH(CH$_3$)$_2$ | H |
| 4-OCF$_3$ | CH$_2$ | —C(CH$_3$)$_3$ | H |
| 4-Cl | CH$_2$ | cyclopropyl | H |
| 4-Cl | CH$_2$ | 2-chlorocyclopropyl | H |
| 4-Cl | CH$_2$ | cyclopentyl | H |
| 4-Cl | CH$_2$ | cyclohexyl | H |
| 2,4,6-Cl$_3$ | CH$_2$ | —CH$_3$ | H |
| 4-C$_6$H$_5$ | CH$_2$ | —CH$_3$ | H |
| 4-O-C$_6$H$_5$ | —CH$_2$ | —CH$_3$ | H |
| 4-OCF$_3$ | CH$_2$ | —CH$_3$ | H |

TABLE 7

(Ii)

$$\text{X}^4_r\text{-C}_6\text{H}_4\text{-Y}^2\text{-CH-CH(OH)-R}^{12}\text{-N(imidazole-2-S-R)}$$

| $X^4_r$ | $R^{12}$ | R | $Y^2$ |
|---|---|---|---|
| 2,4-Cl$_2$ | phenyl | —CH$_3$ | O |
| 4-Cl | phenyl | —CH$_3$ | O |
| 4-Br | —C(CH$_3$)$_3$ | —CH$_3$ | O |
| — | —C(CH$_3$)$_3$ | —CH$_3$ | O |
| 4-C(CH$_3$)$_3$ | —C(CH$_3$)$_3$ | —CH$_3$ | O |
| 2-Cl | —C(CH$_3$)$_3$ | —CH$_3$ | O |
| 3-Cl | —C(CH$_3$)$_3$ | —CH$_3$ | O |
| 4-F | —C(CH$_3$)$_3$ | —CH$_3$ | O |
| 4-C$_6$H$_5$ | —C(CH$_3$)$_3$ | —CH$_3$ | O |

TABLE 7-continued (Ii)

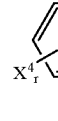

| $X^4_r$ | $R^{12}$ | R | $Y^2$ |
|---|---|---|---|
| 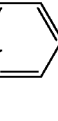 2- | —C(CH₃)₃ | —CH₃ | O |
| 2,4-Cl₂ | —C(CH₃)₃ | —CH₃ | O |
| 2-CH₃, 4-Cl | —C(CH₃)₃ | —CH₃ | O |
| 3,4-(CH₃)₂ | —C(CH₃)₃ | —CH₃ | O |
| 2,4,5-Cl₃ | —C(CH₃)₃ | —CH₃ | O |
| 4-Cl | —CH₃ | —CH₃ | O |
| 4-Cl | —CH₂—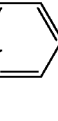 | —CH₃ | O |
| 4-CF₃ | —C(CH₃)₃ | —CH₃ | O |
| 4-OCF₃ | —C(CH₃)₃ | —CH₃ | O |
| 2-OCHF₂ | —C(CH₃)₃ | —CH₃ | O |
| 4-OCH₃ | —C(CH₃)₃ | —CH₃ | O |
| 2,4-Cl₂ | 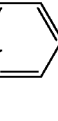 | H | O |
| 4-Cl | 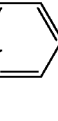 | H | O |
| 4-Br | —C(CH₃)₃ | H | O |
| — | —C(CH₃)₃ | H | O |
| 4-C(CH₃)₃ | —C(CH₃)₃ | H | O |
| 2-Cl | —C(CH₃)₃ | H | O |
| 3-Cl | —C(CH₃)₃ | H | O |
| 4-F | —C(CH₃)₃ | H | O |
| 4-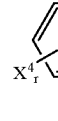 | —C(CH₃)₃ | H | O |
| 2-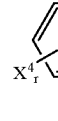 | —C(CH₃)₃ | H | O |
| 2,4-Cl₂ | —C(CH₃)₃ | H | O |
| 2-CH₃, 4-Cl | —C(CH₃)₃ | H | O |
| 3,4-(CH₃)₂ | —C(CH₃)₃ | H | O |
| 2,4,5-Cl₃ | —C(CH₃)₃ | H | O |
| 4-Cl | —CH₃ | H | O |
| 4-Cl | —CH₂—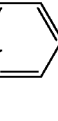 | H | O |
| 4-CF₃ | —C(CH₃)₃ | H | O |
| 4-OCF₃ | —C(CH₃)₃ | H | O |
| 2-OCHF₂ | —C(CH₃)₃ | H | O |
| 4-OCH₃ | —C(CH₃)₃ | H | O |

TABLE 7-continued (Ii)

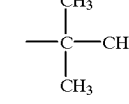

| $X^4_r$ | $R^{12}$ | R | $Y^2$ |
|---|---|---|---|
| 4-Cl | 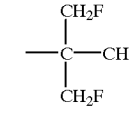 (C(CH₃)₂CH₂F with CH₃) | —CH₃ | O |
| 4-Cl | 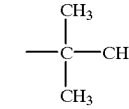 (C(CH₂F)₂CH₃) | —CH₃ | O |
| 4-Cl | 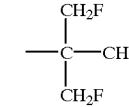 (C(CH₃)₂CH₂F) | H | O |
| 4-Cl | 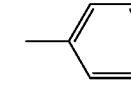 (C(CH₂F)₂CH₃) | H | O |
| 2,4-Cl₂ | 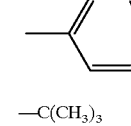 | —CH₃ | CH₂ |
| 4-Cl | 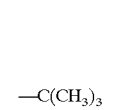 | —CH₃ | CH₂ |
| 4-Br | —C(CH₃)₃ | —CH₃ | CH₂ |
| — | —C(CH₃)₃ | —CH₃ | CH₂ |
| 4-C(CH₃)₃ | —C(CH₃)₃ | —CH₃ | CH₂ |
| 2-Cl | —C(CH₃)₃ | —CH₃ | CH₂ |
| 3-Cl | —C(CH₃)₃ | —CH₃ | CH₂ |
| 4-F | —C(CH₃)₃ | —CH₃ | CH₂ |
| 4-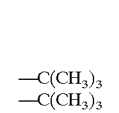 | —C(CH₃)₃ | —CH₃ | CH₂ |
| 2-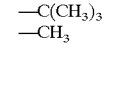 | —C(CH₃)₃ | —CH₃ | CH₂ |
| 2,4-Cl₂ | —C(CH₃)₃ | —CH₃ | CH₂ |
| 2-CH₃, 4-Cl | —C(CH₃)₃ | —CH₃ | CH₂ |
| 3,4-(CH₃)₂ | —C(CH₃)₃ | —CH₃ | CH₂ |
| 2,4,5-Cl₃ | —C(CH₃)₃ | —CH₃ | CH₂ |
| 4-Cl | —CH₃ | —CH₃ | CH₂ |
| 4-Cl | —CH₂— (phenyl) | —CH₃ | CH₂ |

TABLE 7-continued (Ii)

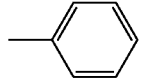

| $X^4_r$ | $R^{12}$ | R | $Y^2$ |
|---|---|---|---|
| 4-CF₃ | —C(CH₃)₃ | —CH₃ | CH₂ |
| 4-OCF₃ | —C(CH₃)₃ | —CH₃ | CH₂ |
| 2-OCHF₂ | —C(CH₃)₃ | —CH₃ | CH₂ |
| 4-OCH₃ | —C(CH₃)₃ | —CH₃ | CH₂ |
| 2,4-Cl₂ | 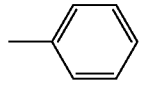 | H | CH₂ |
| 4-Cl | 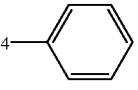 | H | CH₂ |
| 4-Br | —C(CH₃)₃ | H | CH₂ |
| — | —C(CH₃)₃ | H | CH₂ |
| 4-C(CH₃)₃ | —C(CH₃)₃ | H | CH₂ |
| 2-Cl | —C(CH₃)₃ | H | CH₂ |
| 3-Cl | —C(CH₃)₃ | H | CH₂ |
| 4-F | —C(CH₃)₃ | H | CH₂ |
| 4-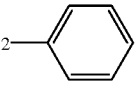 | —C(CH₃)₃ | H | CH₂ |
| 2-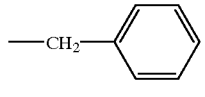 | —C(CH₃)₃ | H | CH₂ |
| 2,4-Cl₂ | —C(CH₃)₃ | H | CH₂ |
| 2-CH₃, 4-Cl | —C(CH₃)₃ | H | CH₂ |
| 3,4-(CH₃)₂ | —C(CH₃)₃ | H | CH₂ |
| 2,4,5-Cl₃ | —C(CH₃)₃ | H | CH₂ |
| 4-Cl | —CH₃ | H | CH₂ |
| 4-Cl | 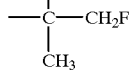 | H | CH₂ |
| 4-CF₃ | —C(CH₃)₃ | H | CH₂ |
| 4-OCF₃ | —C(CH₃)₃ | H | CH₂ |
| 2-OCHF₂ | —C(CH₃)₃ | H | CH₂ |
| 4-OCH₃ | —C(CH₃)₃ | H | CH₂ |
| 4-Cl | 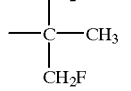 | —CH₃ | CH₂ |
| 4-Cl | 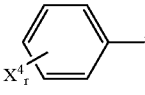 | —CH₃ | CH₂ |

TABLE 7-continued (Ii)

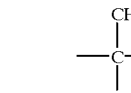

| $X^4_r$ | $R^{12}$ | R | $Y^2$ |
|---|---|---|---|
| 4-Cl | 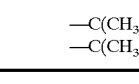 | H | CH₂ |
| 4-Cl | 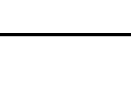 | H | CH₂ |
| 4-Cl | —C(CH₃)₃ | —CH₃ | O |
| 4-Cl | —C(CH₃)₃ | H | O |

TABLE 8

(Ik)

| $X^5_s$ | A | R |
|---|---|---|
| 2,4-Cl₂ | —(CH₂)₃— | —CH₃ |
| 2,4-Cl₂ | —(CH₂)₂— | —CH₃ |
| 4-Cl | 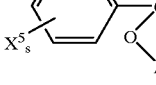 | —CH₃ |
| 4-CF₃ |  | —CH₃ |
| 2-Cl, 4-O——Cl | —CH₂—CH₂— | —CH₃ |
| 2-Cl, 4-O—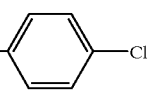—Cl | 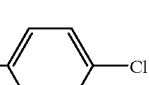 | —CH₃ |
| 4-F |  | —CH₃ |
| 4-OCF₃ |  | —CH₃ |

TABLE 8-continued

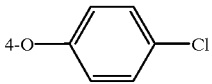

(Ik)

| $X^5_s$ | A | R |
|---|---|---|
| 2,4-$F_2$ | —$CH_2$—CH($C_3H_7$-n)— | —$CH_3$ |
| 2-OCH$F_2$ | —$CH_2$—CH($C_3H_7$-n)— | —$CH_3$ |
| 2-Cl, 4-O-C$_6$H$_4$-Cl | —(CH$_2$)$_3$— | —$CH_3$ |
| 2,4,6-Cl$_3$ | —$CH_2$—CH($C_3H_7$-n)— | —$CH_3$ |
| — | —$CH_2$—CH($C_3H_7$-n)— | —$CH_3$ |
| 2,4-$F_2$ | —$CH_2$—CH(CH$_3$)— | —$CH_3$ |
| 2-Cl, 4-O-C$_6$H$_4$-Cl | —$CH_2$—CH(CH$_3$)— | —$CH_3$ |
| 2,4-Cl$_2$ | —CH(CH$_3$)—CH(CH$_3$)— | —$CH_3$ |
| 2-Cl, 4-O-C$_6$H$_4$-Cl | —CH(CH$_3$)—CH(CH$_3$)— | —$CH_3$ |
| 2,4-Cl$_2$ | —$CH_2$—CH(F)— | —$CH_3$ |
| 2-Cl, 4-O-C$_6$H$_4$-Cl | —$CH_2$—CH($C_4H_9$-n)— | —$CH_3$ |
| 2,4-Cl$_2$ | —$CH_2$—CH($C_2H_5$)— | —$CH_3$ |
| 2,4-Cl$_2$ | —(CH$_2$)$_3$— | H |
| 2,4-Cl$_2$ | —(CH$_2$)$_2$— | H |

TABLE 8-continued

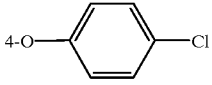

(Ik)

| $X^5_s$ | A | R |
|---|---|---|
| 4-Cl | —$CH_2$—CH(CH$_3$)— | H |
| 4-CF$_3$ | —$CH_2$—CH($C_3H_7$-n)— | H |
| 2-Cl, 4-O-C$_6$H$_4$-Cl | —$CH_2$—$CH_2$— | H |
| 2-Cl, 4-O-C$_6$H$_4$-Cl | —$CH_2$—CH($C_2H_5$)— | H |
| 4-F | —$CH_2$—CH($C_3H_7$-n)— | H |
| 4-OCF$_3$ | —$CH_2$—CH($C_3H_7$-n)— | H |
| 2,4-$F_2$ | —$CH_2$—CH($C_3H_7$-n)— | H |
| 2-OCH$F_2$ | —$CH_2$—CH($C_3H_7$-n)— | H |
| 2-Cl, 4-O-C$_6$H$_4$-Cl | —(CH$_2$)$_3$— | H |
| 2,4,6-Cl$_3$ | —$CH_2$—CH($C_3H_7$-n)— | H |
| — | —$CH_2$—CH($C_3H_7$-n)— | H |
| 2,4-$F_2$ | —$CH_2$—CH(CH$_3$)— | H |
| 2-Cl, 4-O-C$_6$H$_4$-Cl | —$CH_2$—CH(CH$_3$)— | H |

TABLE 8-continued (Ik)

[Structure: phenyl with X⁵_s substituents, connected via C(O-A-O) ring (dioxetane) and CH₂ to N of imidazole with 2-S-R]

| X⁵_s | A | R |
|---|---|---|
| 2,4-Cl₂ | —CH(CH₃)—CH(CH₃)— | H |
| 2-Cl, 4-O-(4-chlorophenyl) | —CH(CH₃)—CH(CH₃)— | H |
| 2,4-Cl₂ | —CH₂—CH(F)— | H |
| 2-Cl, 4-O-(4-chlorophenyl) | —CH₂—CH(C₄H₉-n)— | H |
| 2,4-Cl₂ | —CH₂—CH(C₂H₅)— | H |
| 2,4-Cl₂ | —CH₂—CH(C₃H₇-n)— | —CH₃ |
| 2,4-Cl₂ | —CH₂—CH(C₃H₇-n)— | H |

TABLE 9

(Im)

[Structure: phenyl with X⁶_t substituents, CH(R¹³) group, CH₂ connected to N of imidazole with 2-S-R]

| X⁶_t | R¹³ | R |
|---|---|---|
| 2,4-Cl₂ | —CH₃ | —CH₃ |
| 2,4-Cl₂ | —C₂H₅ | —CH₃ |
| 2,4-Cl₂ | —CH(CH₃)₂ | —CH₃ |
| 4-Cl | —C₃H₇-n | —CH₃ |
| 2,4-Cl₂ | —C₄H₉-n | —CH₃ |
| 2,4-Cl₂ | —CH(CH₃)—C₂H₅ | —CH₃ |
| 2,4-Cl₂ | —C(CH₃)₃ | —CH₃ |
| 2-Cl | —C₃H₇-n | —CH₃ |

TABLE 9-continued (Im)

| X⁶_t | R¹³ | R |
|---|---|---|
| 2-OCF₃ | —C₃H₇-n | —CH₃ |
| 4-CF₃ | —C₃H₇-n | —CH₃ |
| 4-CH₃ | —C₃H₇-n | —CH₃ |
| 2,4,6-Cl₃ | —C₃H₇-n | —CH₃ |
| 2,4-Cl₂ | chlorocyclopropyl | —CH₃ |
| 4-F | —C₃H₇-n | —CH₃ |
| 2,4-Cl₂ | fluorocyclopropyl | —CH₃ |
| 2,4-Cl₂ | cyclopropyl | —CH₃ |
| 2,4-Cl₂ | cyclopentyl | —CH₃ |
| 2,4-Cl₂ | cyclohexyl | —CH₃ |
| 2,4-Cl₂ | —CH₂-cyclohexyl | —CH₃ |
| 2,4-Cl₂ | —CH(CH₃)-cyclopropyl | —CH₃ |
| 2,4-Cl₂ | 4-chlorophenyl | —CH₃ |
| 2,4-Cl₂ | 4-fluorophenyl | —CH₃ |
| 2,4-Cl₂ | —CH₂-(4-chlorophenyl) | —CH₃ |
| 2,4-Cl₂ | —CH₂-(4-fluorophenyl) | —CH₃ |
| 2,4-Cl₂ | —CH₂—O—CF₂—CHF₂ | —CH₃ |
| 2,4-Cl₂ | —CH₂—O—CF₂—CH₃ | —CH₃ |
| 4-Cl | —CH₂—O—CF₂—CHF₂ | —CH₃ |
| 2,4-Cl₂ | —CH₂—O—CF₃ | —CH₃ |

TABLE 9-continued (Im)

[Structure: phenyl group with $X^6_t$ substituents, connected via CH(R^13)-CH2 to N of imidazole, with 2-position S-R]

| $X^6_t$ | $R^{13}$ | R |
|---|---|---|
| 4-F | —CH$_2$—O—CF$_2$—CHF$_2$ | —CH$_3$ |
| 2-Cl | —CH$_2$—O—CF$_2$—CHF$_2$ | —CH$_3$ |
| 2,4-Cl$_2$ | —CH$_3$ | H |
| 2,4-Cl$_2$ | —C$_2$H$_5$ | H |
| 2,4-Cl$_2$ | —CH(CH$_3$)$_2$ | H |
| 4-Cl | —C$_3$H$_7$-n | H |
| 2,4-Cl$_2$ | —C$_4$H$_9$-n | H |
| 2,4-Cl$_2$ | —CH(CH$_3$)—C$_2$H$_5$ | H |
| 2,4-Cl$_2$ | —C(CH$_3$)$_3$ | H |
| 2-Cl | —C$_3$H$_7$-n | H |
| 2-OCF$_3$ | —C$_3$H$_7$-n | H |
| 4-CF$_3$ | —C$_3$H$_7$-n | H |
| 4-CH$_3$ | —C$_3$H$_7$-n | H |
| 2,4,6-Cl$_3$ | —C$_3$H$_7$-n | H |
| 2,4-Cl$_2$ | cyclopropyl-Cl | H |
| 4-F | —C$_3$H$_7$-n | H |
| 2,4-Cl$_2$ | cyclopropyl-F | H |
| 2,4-Cl$_2$ | cyclopropyl | H |
| 2,4-Cl$_2$ | cyclopentyl | H |
| 2,4-Cl$_2$ | cyclohexyl | H |
| 2,4-Cl$_2$ | —CH$_2$-cyclohexyl | H |
| 2,4-Cl$_2$ | —CH(CH$_3$)-cyclopropyl | H |
| 2,4-Cl$_2$ | —(4-Cl-phenyl) | H |
| 2,4-Cl$_2$ | —(4-F-phenyl) | H |

TABLE 9-continued (Im)

| $X^6_t$ | $R^{13}$ | R |
|---|---|---|
| 2,4-Cl$_2$ | —CH$_2$—(4-Cl-phenyl) | H |
| 2,4-Cl$_2$ | —CH$_2$—(4-F-phenyl) | H |
| 2,4-Cl$_2$ | —CH$_2$—O—CF$_2$—CHF$_2$ | H |
| 2,4-Cl$_2$ | —CH$_2$—O—CF$_2$—CH$_3$ | H |
| 4-Cl | —CH$_2$—O—CF$_2$—CHF$_2$ | H |
| 2,4-Cl$_2$ | —CH$_2$—O—CF$_3$ | H |
| 4-F | —CH$_2$—O—CF$_2$—CHF$_2$ | H |
| 2-Cl | —CH$_2$—O—CF$_2$—CHF$_2$ | H |
| 2,4-Cl$_2$ | —CH$_2$—CF$_3$ | —CH$_3$ |
| 2,4-Cl$_2$ | —CF$_2$—CF$_3$ | —CH$_3$ |
| 2,4-Cl$_2$ | —C$_3$H$_7$-n | —CH$_3$ |
| 2,4-Cl$_2$ | —C$_3$H$_7$-n | H |

TABLE 10

(In)

[Structure: phenyl with $X^7_u$ substituents connected via $Y^3$—CH(C(=O)R^{14})— to N of imidazole with 2-position S-R]

| $X^7_u$ | $R^{14}$ | R | $Y^3$ |
|---|---|---|---|
| 2,4-Cl$_2$ | phenyl | —CH$_3$ | O |
| 4-Cl | phenyl | —CH$_3$ | O |
| 4-Br | —C(CH$_3$)$_3$ | —CH$_3$ | O |
| — | —C(CH$_3$)$_3$ | —CH$_3$ | O |
| 4-C(CH$_3$)$_3$ | —C(CH$_3$)$_3$ | —CH$_3$ | O |
| 2-Cl | —C(CH$_3$)$_3$ | —CH$_3$ | O |
| 3-Cl | —C(CH$_3$)$_3$ | —CH$_3$ | O |
| 4-F | —C(CH$_3$)$_3$ | —CH$_3$ | O |
| 4-phenyl | —C(CH$_3$)$_3$ | —CH$_3$ | O |

TABLE 10-continued (In)

| $X^7_u$ | $R^{14}$ | R | $Y^3$ |
|---|---|---|---|
| 2-phenyl | —C(CH₃)₃ | —CH₃ | O |
| 2,4-Cl₂ | —C(CH₃)₃ | —CH₃ | O |
| 2-CH₃, 4-Cl | —C(CH₃)₃ | —CH₃ | O |
| 3,4-(CH₃)₂ | —C(CH₃)₃ | —CH₃ | O |
| 2,4,5-Cl₃ | —C(CH₃)₃ | —CH₃ | O |
| 4-Cl | —CH₃ | —CH₃ | O |
| 4-Cl | —CH₂-phenyl | —CH₃ | O |
| 4-CF₃ | —C(CH₃)₃ | —CH₃ | O |
| 4-OCF₃ | —C(CH₃)₃ | —CH₃ | O |
| 2-OCHF₂ | —C(CH₃)₃ | —CH₃ | O |
| 4-OCH₃ | —C(CH₃)₃ | —CH₃ | O |
| 2,4-Cl₂ | phenyl | H | O |
| 4-Cl | phenyl | H | O |
| 4-Br | —C(CH₃)₃ | H | O |
| — | —C(CH₃)₃ | H | O |
| 4-C(CH₃)₃ | —C(CH₃)₃ | H | O |
| 2-Cl | —C(CH₃)₃ | H | O |
| 3-Cl | —C(CH₃)₃ | H | O |
| 4-F | —C(CH₃)₃ | H | O |
| 4-phenyl | —C(CH₃)₃ | H | O |
| 2-phenyl | —C(CH₃)₃ | H | O |
| 2,4-Cl₂ | —C(CH₃)₃ | H | O |
| 2-CH₃, 4-Cl | —C(CH₃)₃ | H | O |
| 3,4-(CH₃)₂ | —C(CH₃)₃ | H | O |
| 2,4,5-Cl₃ | —C(CH₃)₃ | H | O |
| 4-Cl | —CH₃ | H | O |
| 4-Cl | —CH₂-phenyl | H | O |
| 4-CF₃ | —C(CH₃)₃ | H | O |
| 4-OCF₃ | —C(CH₃)₃ | H | O |
| 2-OCHF₂ | —C(CH₃)₃ | H | O |
| 4-OCH₃ | —C(CH₃)₃ | H | O |
| 4-Cl | —C(CH₃)₂CH₂F | —CH₃ | O |
| 4-Cl | —C(CH₂F)₂CH₃ | —CH₃ | O |
| 4-Cl | —C(CH₃)₂CH₂F | H | O |
| 4-Cl | —C(CH₃)(CH₂F)₂ | H | O |
| 2,4-Cl₂ | phenyl | —CH₃ | CH₂ |
| 4-Cl | phenyl | —CH₃ | CH₂ |
| 4-Br | —C(CH₃)₃ | —CH₃ | CH₂ |
| — | —C(CH₃)₃ | —CH₃ | CH₂ |
| 4-C(CH₃)₃ | —C(CH₃)₃ | —CH₃ | CH₂ |
| 2-Cl | —C(CH₃)₃ | —CH₃ | CH₂ |
| 3-Cl | —C(CH₃)₃ | —CH₃ | CH₂ |
| 4-F | —C(CH₃)₃ | —CH₃ | CH₂ |
| 4-phenyl | —C(CH₃)₃ | —CH₃ | CH₂ |
| 2-phenyl | —C(CH₃)₃ | —CH₃ | CH₂ |
| 2,4-Cl | —C(CH₃)₃ | —CH₃ | CH₂ |
| 2-CH₃, 4-Cl | —C(CH₃)₃ | —CH₃ | CH₂ |
| 3,4-(CH₃)₂ | —C(CH₃)₃ | —CH₃ | CH₂ |
| 2,4,5-Cl₃ | —C(CH₃)₃ | —CH₃ | CH₂ |
| 4-Cl | —CH₃ | —CH₃ | CH₂ |
| 4-Cl | —CH₂-phenyl | —CH₃ | CH₂ |

TABLE 10-continued (In)

[Structure: phenyl with $X^7_u$ substituents connected via $Y^3$-CH to C(=O)$R^{14}$, with N-imidazole bearing 2-S-R group]

| $X^7_u$ | $R^{14}$ | R | $Y^3$ |
|---|---|---|---|
| 4-CF$_3$ | —C(CH$_3$)$_3$ | —CH$_3$ | CH$_2$ |
| 4-OCF$_3$ | —C(CH$_3$)$_3$ | —CH$_3$ | CH$_2$ |
| 2-OCHF$_2$ | —C(CH$_3$)$_3$ | —CH$_3$ | CH$_2$ |
| 4-OCH$_3$ | —C(CH$_3$)$_3$ | —CH$_3$ | CH$_2$ |
| 2,4-Cl$_2$ | phenyl | H | CH$_2$ |
| 4-Cl | phenyl | H | CH$_2$ |
| 4-Br | —C(CH$_3$)$_3$ | H | CH$_2$ |
| — | —C(CH$_3$)$_3$ | H | CH$_2$ |
| 4-C(CH$_3$)$_3$ | —C(CH$_3$)$_3$ | H | CH$_2$ |
| 2-Cl | —C(CH$_3$)$_3$ | H | CH$_2$ |
| 3-Cl | —C(CH$_3$)$_3$ | H | CH$_2$ |
| 4-F | —C(CH$_3$)$_3$ | H | CH$_2$ |
| 4-phenyl | —C(CH$_3$)$_3$ | H | CH$_2$ |
| 2-phenyl | —C(CH$_3$)$_3$ | H | CH$_2$ |
| 2,4-Cl$_2$ | —C(CH$_3$)$_3$ | H | CH$_2$ |
| 2-CH$_3$, 4-Cl | —C(CH$_3$)$_3$ | H | CH$_2$ |
| 3,4-(CH$_3$)$_2$ | —C(CH$_3$)$_3$ | H | CH$_2$ |
| 2,4,5-Cl$_3$ | —C(CH$_3$)$_3$ | H | CH$_2$ |
| 4-Cl | —CH$_3$ | H | CH$_2$ |
| 4-Cl | —CH$_2$-phenyl | H | CH$_2$ |
| 4-CF$_3$ | —C(CH$_3$)$_3$ | H | CH$_2$ |
| 4-OCF$_3$ | —C(CH$_3$)$_3$ | H | CH$_2$ |
| 2-OCHF$_2$ | —C(CH$_3$)$_3$ | H | CH$_2$ |
| 4-OCH$_3$ | —C(CH$_3$)$_3$ | H | CH$_2$ |
| 4-Cl | —C(CH$_3$)(CH$_2$F)(CH$_3$) | —CH$_3$ | CH$_2$ |
| 4-Cl | —C(CH$_2$F)(CH$_3$)(CH$_2$F) | —CH$_3$ | CH$_2$ |
| 4-Cl | —C(CH$_3$)(CH$_2$F)(CH$_3$) | H | CH$_2$ |
| 4-Cl | —C(CH$_2$F)(CH$_3$)(CH$_2$F) | H | CH$_2$ |
| 4-Cl | —C(CH$_3$)$_3$ | —CH$_3$ | O |
| 4-Cl | —C(CH$_3$)$_3$ | H | O |

TABLE 11

(Ip)

[Structure: phenyl with $X^8_v$ substituents connected via $Y^3$-C(CN)($R^{15}$)-CH$_2$- to N-imidazole bearing 2-S-R group]

| $X^8_v$ | $R^{15}$ | R |
|---|---|---|
| 4-Cl | —C$_4$H$_9$-n | —CH$_3$ |
| 2-Cl | —C$_4$H$_9$-n | —CH$_3$ |
| 2,4-Cl$_2$ | —C$_4$H$_9$-n | —CH$_3$ |
| 4-Br | —C$_4$H$_9$-n | —CH$_3$ |
| 4-F | —C$_4$H$_9$-n | —CH$_3$ |
| 4-C(CH$_3$)$_3$ | —C$_4$H$_9$-n | —CH$_3$ |
| 4-phenyl | —C$_4$H$_9$-n | —CH$_3$ |
| 4-Cl | —C(CH$_3$)$_3$ | —CH$_3$ |
| 2-Cl | —C(CH$_3$)$_3$ | —CH$_3$ |
| 2,4-Cl$_2$ | —C(CH$_3$)$_3$ | —CH$_3$ |
| 2,4,6-Cl$_3$ | —C(CH$_3$)$_3$ | —CH$_3$ |
| 4-CF$_3$ | —C(CH$_3$)$_3$ | —CH$_3$ |
| 2-OCHF$_2$ | —C(CH$_3$)$_3$ | —CH$_3$ |
| 4-Cl | —C(CH$_3$)(CH$_2$F)(CH$_3$) | —CH$_3$ |
| 4-Cl | —C(CH$_2$F)(CH$_3$)(CH$_2$F) | —CH$_3$ |

TABLE 11-continued (Ip)

structure: X⁸ᵥ-phenyl-Y³-C(CN)(R¹⁵)-CH₂-N(imidazole with 2-S-R)

| X⁸ᵥ | R¹⁵ | R |
|---|---|---|
| 4-Cl | —CH₂—C₆H₄—Cl (4-Cl) | —CH₃ |
| 4-Cl | —CH(CH₃)—C₆H₄—Cl (4-Cl) | —CH₃ |
| 4-Cl | —C₆H₄—Cl (4-Cl) | —CH₃ |
| 4-Cl | —CH₂—CH₂—C₆H₄—Cl (4-Cl) | —CH₃ |
| — | —CH₂—CH₂—C₆H₄—F (4-F) | —CH₃ |
| 4-Cl | —C₄H₉-n | H |
| 2-Cl | —C₄H₉-n | H |
| 2,4-Cl₂ | —C₄H₉-n | H |
| 4-Br | —C₄H₉-n | H |
| 4-F | —C₄H₉-n | H |
| 4-C(CH₃)₃ | —C₄H₉-n | H |
| 4-phenyl | —C₄H₉-n | H |
| 4-Cl | —C(CH₃)₃ | H |
| 2-Cl | —C(CH₃)₃ | H |
| 2,4-Cl₂ | —C(CH₃)₃ | H |
| 2,4,6-Cl₃ | —C(CH₃)₃ | H |
| 4-CF₃ | —C(CH₃)₃ | H |
| 2-OCHF₂ | —C(CH₃)₃ | H |
| 4-Cl | —C(CH₃)(CH₂F)(CH₃) | H |
| 4-Cl | —C(CH₂F)(CH₃)(CH₂F) | H |

TABLE 11-continued (Ip)

| X⁸ᵥ | R¹⁵ | R |
|---|---|---|
| 4-Cl | —CH₂—C₆H₄—Cl (4-Cl) | H |
| 4-Cl | —CH(CH₃)—C₆H₄—Cl (4-Cl) | H |
| 4-Cl | —C₆H₄—Cl (4-Cl) | H |
| 4-Cl | —CH₂—CH₂—C₆H₄—Cl (4-Cl) | H |
| — | —CH₂—CH₂—C₆H₄—Cl (4-Cl) | H |
| — | —CH₂—CH₂—C₆H₄—F (4-F) | H |
| — | —CH₂—CH₂—C₆H₄—Cl (4-Cl) | —CH₃ |

If 2-(1-chloro-cyclopropyl)-1-(2-chloro-phenyl)-3-(imidazol-1-yl)-propan-2-ol is used as the starting material, n-butyl-lithium as the strong base and sulphur powder as reactant, the course of the first step of the process according to the invention (variant a) can be illustrated by the following scheme:

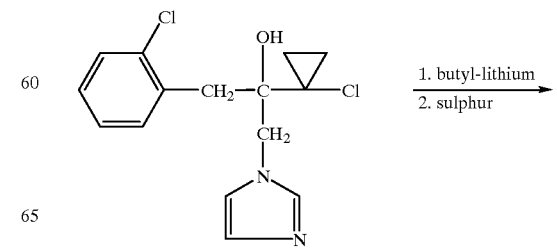

1. butyl-lithium
2. sulphur

-continued

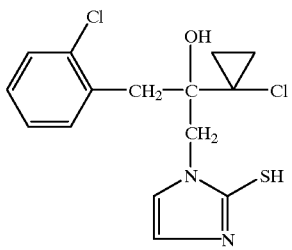

If 2-(1-chloro-cyclopropyl)-1-(2-chloro-phenyl)-3-(imidazol-1-yl)-propan-2-ol is used as the starting material, sulphur powder as reactant and N-methyl-pyrrolidone as diluent, the course of the first step of the process according to the invention (variant b) can be illustrated by the following scheme:

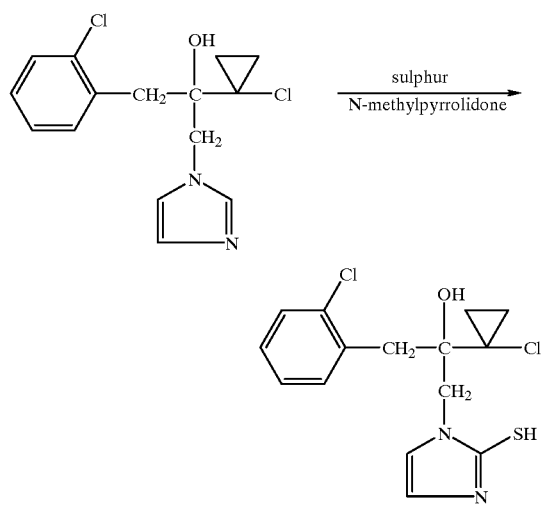

If 2-(1-chloro-cyclopropyl)-1-(2-chlorophenyl)-3-(2-mercapto-imidazol-1-yl)-propan-2-ol is used as the starting material and methyl iodide as reactant, the course of the second step of the process according to the invention can be illustrated by the following scheme:

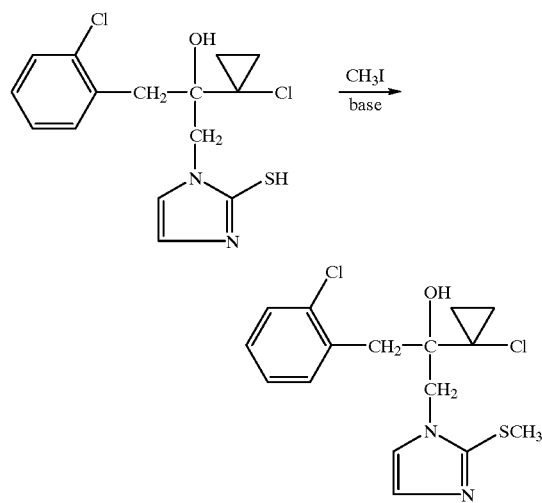

Formula (II) provides a general definition of the imidazoles required as starting materials for carrying out the process according to the invention. In this formula, $R^1$ preferably has those meanings which have already been mentioned in connection with the description of the substances of the formula (I) according to the invention as being preferred for this radical.

The imidazoles of the formula (II) are known or can be prepared by known methods (cf. EP-A 0 015 756, EP-A 0 040 345, EP-A 0 052 424, EP-A 0 061 835, EP-A 0 297 345, EP-A 0 094 564, EP-A 0 196 038, EP-A 0 267 778, EP-A 0 378 953, EP-A 0 044 605, EP-A 0 069 442, EP-A 0 055 833, EP-A 0 301 393, DE-A 2 324 010, DE-A 2 737 489, DE-A 2 551 560, EP-A 0 065 485, DE-A 2 735 872, EP-A 0 234 242, DE-A 2 201 063, EP-A 0 145 294 and DE-A 3 721 786).

Suitable bases for carrying out the first step of the process according to the invention (variant a) are all strong alkali metal bases which are customary for such reactions. The following can preferably be used: n-butyl-lithium, lithium diisopropyl-amide, sodium hydride, sodium amide or else potassium tert-butoxide as a mixture with tetramethylethylene-diamine (=TMEDA).

Suitable diluents for carrying out the first step of the process according to the invention (variant a) are all inert organic solvents which are customary for such reactions. The following can preferably be used: ethers such as tetrahydrofuran, dioxane, diethyl ether and 1,2-dimethoxyethane, furthermore liquid ammonia or else strongly polar solvents such as dimethyl sulphoxide.

Sulphur is preferably employed in the form of a powder. Water, if appropriate in the presence of an acid, is used for the hydrolysis when carrying out the first step of the process according to the invention (variant a). Suitable for this purpose are all inorganic or organic acids which are customary for such reactions. The following can preferably be used: acetic acid, dilute sulphuric acid and dilute hydrochloric acid. However, it is also possible to carry out the hydrolysis with aqueous ammonium chloride solution.

When carrying out the first step of the process according to the invention (variant a), the reaction temperatures can be varied within a certain range. In general, the process is carried out at temperatures between −70° C. and +20° C., preferably between −70° C. and 0° C.

All steps of the process according to the invention are generally carried out under atmospheric pressure. However, it is also possible to carry out these steps under elevated or reduced pressure. In particular, the first step of the process according to the invention in accordance with variant (b) may be carried out under elevated pressure.

When carrying out the first step of the process according to the invention in accordance with variant (a), 2 to 3 equivalents, preferably 2.0 to 2.5 equivalents, of strong base and subsequently an equivalent amount or else an excess of sulphur are generally employed per mole of imidazole of the formula (II). The reaction can be carried out under protective gas atmosphere, for example under nitrogen or argon. Working-up is carried out by customary methods. In general, a procedure is followed in which the reaction mixture is extracted with an organic solvent which is sparingly soluble in water, the combined organic phases are dried and concentrated, and, if appropriate, the residue which remains is purified by recrystallization and/or chromatography.

When carrying out the first step of the process according to the invention in accordance with variant (b), suitable diluents are all organic solvents of high boiling point which are customary for such reactions. The following can preferably be used: amides such as dimethylformamide and dimethylacetamide, furthermore heterocyclic compounds such as N-methyl-pyrrolidone, or else ethers such as diphenyl ether.

When carrying out the first step of the process according to the invention in accordance with variant (b), sulphur is, again, generally employed in the form of a powder. If appropriate, a treatment with water and, if appropriate, with acid may be carried out after the reaction. This treatment is carried out like the hydrolysis when carrying out the first step of the process according to the invention in accordance with variant (a).

When carrying out the first step of the process according to the invention in accordance with variant (b), the reaction temperatures can, again, be varied within a substantial range. In general, the process is carried out at temperatures between 150° C. and 300° C., preferably between 180° C. and 250° C.

When carrying out the first step of the process according to the invention in accordance with variant (b), 1 to 5 mol, preferably 1.5 to 3 mol, of sulphur are generally employed per mole of imidazole of the formula (II). Working-up is carried out by customary methods. In general, a procedure is followed in which the reaction mixture is extracted with an organic solvent which is only sparingly soluble in water, the combined organic phases are dried and concentrated, and, if appropriate, the residue which remains is freed from any impurities which may be present by customary methods, such as recrystallization or chromatography.

The compounds of the formula (Ia) required as starting materials when carrying out the second step of the process according to the invention are substances according to the invention.

Formula (III) provides a general definition of the halogen compounds required as reactants when carrying out the second step of the process according to the invention.

R16 preferably represents methyl, ethyl, n-propyl or isopropyl.

HaI preferably represents chlorine, bromine or iodine.

$R^{16}$ especially preferably represents methyl or ethyl.

HaI especially preferably represents bromine or iodine.

The halogen compounds of the formula (III) are known.

Suitable acid binders for carrying out the second step of the process according to the invention are all customary inorganic or organic bases. The following can preferably be used: alkaline earth metal hydroxides or alkali metal hydroxides such as sodium hydroxide, calcium hydroxide, potassium hydroxide, or else ammonium hydroxide, alkali metal carbonates such as sodium carbonate, potassium carbonate, potassium hydrogen carbonate, sodium hydrogen carbonate, alkali metal acetates or alkaline earth metal acetates such as sodium acetate, potassium acetate, calcium acetate, and tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

Diluents which are suitable for carrying out the second step of the process according to the invention are all inert organic solvents which are customary for such reactions. The following can preferably be used: ethers such as diethyl ether, methyl tert-butyl ether, ethylene glycol dimethyl ether, tetrahydrofuran and dioxane, furthermore nitriles such as acetonitrile, and also strongly polar solvents such as dimethyl sulphoxide or dimethylformamide.

When carrying out the second step of the process according to the invention, the reaction temperatures can be varied within a substantial range. In general, the process is carried out at temperatures between 0° C. and 120° C., preferably between 20° C. and 100° C.

When carrying out the second step of the process according to the invention, 1 to 2 mol of halogen compound of the formula (III) and an equivalent amount or else an excess of acid binder are generally employed per mole of mercapto-imidazolyl derivative of the formula (Ia). Working-up is carried out by customary methods. In general, a procedure is followed in which the reaction mixture is treated with aqueous base and an organic solvent which is sparingly miscible with water, and the organic phase is separated off, dried and concentrated. If appropriate, the product obtained can be freed from any impurities which may be present by customary methods, for example by recrystallization.

The mercapto-imidazolyl derivatives of the formula (I) which can be obtained by the process according to the invention can be converted into acid addition salts or metal salt complexes.

Acids which are suitable for the preparation of acid addition salts of the compounds of the formula (I) are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if appropriate, purified by washing with an inert organic solvent. Metal salts which are suitable for the preparation of metal salt complexes of the compounds of the formula (I) are preferably those which have already been mentioned as preferred metal salts in connection with the description of the metal salt complexes according to the invention.

The metal salt complexes of the compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtration, and, if appropriate, purified by recrystallization.

The active compounds according to the invention exhibit a potent microbicidal action and can be employed in crop protection and in the protection of materials for controlling undesired microorganisms such as fungi and bacteria.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;*

(conidial form: Drechslera, syn: Helminthosporium);
Cochliobolus species, such as *Cochliobolus sativus*;
(conidial form: Drechslera, syn: Helminthosporium);
Uromyces species, such as *Uromyces appendiculatus*;
Puccinia species, such as *Puccinia recondita*;
Tilletia species, such as *Tilletia caries*;
Ustilago species, such as *Ustilago nuda* or *Ustilago avenae*;
Pellicularia species, such as *Pellicularia sasakii*;
Pyricularia species, such as *Pyricularia oryzae*;
Fusarium species, such as *Fusarium culmorum*;
Botrytis species, such as *Botrytis cinerea*;
Septoria species, such as *Septoria nodorum*;
Leptosphaeria species, such as *Leptosphaeria nodorum*;
Cercospora species, such as *Cercospora canescens*;
Altemaria species, such as *Altemaria brassicae*;
Pseudocercosporella species, such as *Pseudocercosporella herpotrichoides*.

The good toleration, by plants, of the active compounds, at the concentrations required for controlling plant diseases, permits treatment of above-ground parts of plants, of vegetative propagation stock and seeds, and of the soil.

The active compounds according to the invention are particularly suitable for controlling *Pyricularia oryzae* and *Pellicularia sasakii* on rice and for controlling cereal diseases such as Pseudocercosporella, Erysiphe and Fusarium species. In addition, the substances according to the invention can be employed very successfully against Venturia and Sphaerotheca. Moreover, they also have a very good in vitro action.

In the protection of materials, the substances according to the invention can be employed for protecting industrial materials against infestation with, and destruction by, undesired microorganisms.

Industrial materials in the present context are understood as meaning non-live materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infested with, or destroyed by, microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids, especially preferably wood. Microorganisms which may be mentioned as being capable of bringing about degradation of, or change in, the industrial materials are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
Altemaria, such as *Altemaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, and ULV cold and hot fogging formulations.

These formulations are produced in a known manner, for example by mixing the active compounds with extenders, that is, liquid solvents, liquefied gases under pressure, and/or solid carriers, optionally with the use of surface-active agents, that is emulsifiers and/or dispersants, and/or foam formers. In the case of the use of water as an extender, organic solvents can, for example, also be used as auxiliary solvents. The main liquid solvents suitable are: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants such as butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as highly-disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxy-methylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%. When used in crop protection, the active compounds according to the invention, as such or in their formulations, can also be used as a mixture with known fungicides, bactericides, acaricides, nematicides or insecticides, for example to widen the spectrum of action or to prevent the build-up of resistance. In many cases, synergistic effects are obtained, i.e. the activity of the mixture is greater than the activity of the individual components.

Examples of suitable components in mixtures are the following substances.

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-dichloro-N-(4-trifluoromethylbenzyl)benzamide;(E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, toiclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds such as herbicides, or with fertilizers and growth regulators, is also possible.

The active compounds can be used as such, in the form of their formulations or as the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method, or to inject the active compound preparation or the active compound itself into the soil. The seed of the plants can also be treated.

For the treatment of parts of plants, the active compound concentrations in the use forms can be varied within a substantial range: they are generally between 1 and 0.0001% by weight, preferably between 0.5 and 0.001% by weight.

For the treatment of seed, amounts of active compound of 0.001 to 50 g, preferably 0.01 to 10 g, are generally required per kilogram of seed.

For the treatment of the soil, active compound concentrations of 0.00001 to 0.1% by weight, preferably 0.0001 to 0.02% by weight, are required at the site of action.

The compositions used for the protection of industrial materials generally comprise the active ingredients in an amount of 1 to 95%, preferably 10 to 75%.

The use concentrations of the active compounds according to the invention depend on the species and the occurrence of the microorganisms to be controlled and on the composition of the material to be protected. The optimal rate can be determined by test series. In general, the use concentrations are in the range from 0.001 to 5% by weight, preferably 0.05 to 1.0% by weight, based on the material to be protected.

The activity and spectrum of action of the active compounds to be used according to the invention in the protection of materials, or of the compositions, concentrates or, quite generally, formulations which can be prepared therefrom, can be increased when, if appropriate, other antimicrobially active compounds, fungicides, bactericides, herbicides, insecticides or other active compounds for widening the spectrum of action or achieving specific effects, such as, for example, an additional protection against insects, are added. These mixtures may have a wider spectrum of action than the compounds according to the invention.

The preparation and use of the substances according to the invention can be seen from the examples which follow.

PREPARATION EXAMPLES

Example 1

(I-1)

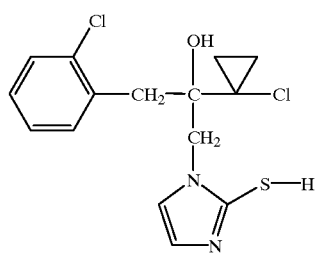

A mixture of 1.55 g (5 mmol) of 2-(1-chloro-cyclopropyl)-1-(2-chloro-phenyl)-3-(imidazol-1-yl)-propan-2-ol, 0.32 g (0.01 gram atom) of sulphur powder and 20 ml of absolute N-methyl-pyrrolidone is heated for 3 hours at 200° C. with stirring. The reaction mixture is subsequently diluted with ethyl acetate and extracted repeatedly by shaking with saturated aqueous ammonium chloride solution. Then, the organic phase is dried over sodium sulphate and concentrated under reduced pressure. The product which remains is chromatographed on silica gel using petroleum ether/ethyl acetate=1:1 as mobile phase. After the eluate has been concentrated, 0.6 g (35% of theory) of 2-(1-chloro-cyclopropyl)-1-(2-chloro-phenyl)-3-(2-mercapto-imidazol-1-yl)-propan-2-ol is obtained in the form of a solid of melting point 124 to 126° C.

$^1$H NMR spectrum (200 MHz; CDCl$_3$; TMS):δ=0.6–1.1 (m,4H); 3.0 (d,1H); 3.75 (d,1H); 4.4 (AB,2H); 5.15 (OH); 6.7 (1H); 7.05 (1H); 7.2–7.6 (m,4H); 10.25 (1H) ppm.

Preparation of the starting material (II-1)

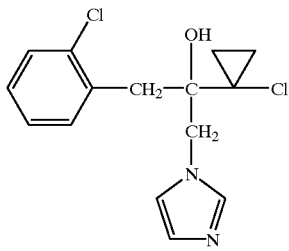

A mixture of 5.56 g (20 mmol) of 3-chloro-2-(1-chloro-cyclopropyl)-1-(2-chloro-phenyl)-propan-2-ol, 1.36 g (20 mmol) of imidazole and 4.15 g (30 mmol) of anhydrous potassium carbonate in 30 ml of absolute dimethylformamide is heated for 23 hours at 100° C. with stirring. The reaction mixture is subsequently diluted with ethyl acetate and extracted repeatedly with saturated aqueous ammonium chloride solution. Then, the organic phase is dried over sodium sulphate and concentrated under reduced pressure. The product which remains is chromatographed on silica gel using ethyl acetate as the mobile phase. After the eluate has been concentrated under reduced pressure, 1.7 g (27% of theory) of 2-(1-chloro-cyclopropyl)-1-(2-chloro-phenyl)-3-(imidazol-1-yl)-propan-2-ol are obtained in the form of a solid of melting point 136 to 139° C.

$^1$H NMR spectrum (400 MHz; CDCl$_3$; TMS):δ=0.5–0.8 (m,4H); 3.3 (d, 1H); 3.45 (d,1H); 4.0 (d,1H); 4.6 (d,1H); 7.0 (m,2H); 7.25–7.5 (m,4H); 7.55 (s,1H) ppm.

Example A

Erysiphe test (barley)/protective

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the given rate of application.

After the spray coating has dried on, the plants are dusted with spores of *Erysiphe graminis* f.sp. hordei.

The plants are placed in a greenhouse at a temperature of approx. 20° C. and a relative atmospheric humidity of approx. 80%, in order to promote the development of powdery mildew pustules.

Evaluation is carried out 7 days after the inoculation. 0% means an efficacy which corresponds to that of the control, while an efficacy of 100% means that no disease is observed.

Active compounds, active compound concentrations and test results can be seen from the table which follows.

TABLE A

Erysiphe test (barley)/protective

| Active compound | Rate of application of active compound in g/ha | Efficacy in % |
|---|---|---|
| According to the invention: | | |
| 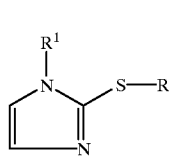 (I-1) | 250 | 83 |

Example B
Sphaerotheca test (cucumber)/protective
Solvent: 47 parts by weight of acetone
Emulsifier: 3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the given rate of application. After the spray coating has dried on, the plants are inoculated with an aqueous spore suspejnsion of *Sphaerotheca fuliginea*. The plants are placed in a greenhouse at approx. 23° C. and at a relative atmospheric humidity of approx. 70%.

Evaluation is carried out 10 days after the inoculation. 0% means an efficacy which corresponds to that of the control, while 100% means that no disease is observed.

Active compounds, active compound concentrations and test results can be seen from the table which follows.

TABLE B

Sphaerotheca test (cucumber)/protective

| Active compound | Rate of application of active compound in g/ha | Efficacy in %, |
|---|---|---|
| According to the invention: | | |
| 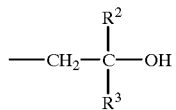 (I-1) | 100 | 77 |

Example C
Venturia test (apple)/protective
Solvent: 47 parts by weight of acetone
Emulsifier: 3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the given rate of application. After the spray coating has dried on, the plants are inoculated with an aqueous conidial suspension of the apple scab causative organism *Venturia inaequalis* and then remain in an incubation cabin at approx. 20° C. and 100% relative atmospheric humidity for 1 day.

The plants are then placed in a greenhouse at 21° C. and a relative atmospheric humidity of approx. 90%.

Evaluation is carried out 12 days after the inoculation. 0% means an efficacy which corresponds to that of the control, while 100% means that no disease is observed.

Active compounds, active compound concentrations and test results can be seen from the table which follows.

TABLE C

Venturia test (apple)/protective

| Active compound | Rate of application of active compound in g/ha | Efficacy in % |
|---|---|---|
| According to the invention: | | |
| (I-1) | 50 | 79 |

What is claimed is:
1. A mercapto-imidazole compound of the formula

(I)

$$\underset{N}{\overset{R^1}{\underset{|}{N}}}\!\!\!\!\!\!\!\!\!\!\!\!-\!\!S\!-\!R$$

wherein
R represents hydrogen or an alkyl having 1 to 4 carbon atoms, and
$R^1$ represents a radical of the formula $$-CH_2-\underset{R^3}{\overset{R^2}{\underset{|}{C}}}-OH$$

wherein
$R^2$ represents straight-chain or branched alkyl having 1 to 6 carbon atoms, which is unsubstituted or monosubstituted to tetrasubstituted by identical or different substituents selected from the group consisting of halogen, alkoxy having 1 to 4 carbon atoms, alkoximino having 1 to 4 carbon atoms in the alkoxy moiety and cycloalkyl having 3 to 7 atoms, or
represents cycloalkyl having 3 to 7 carbon atoms, which is unsubstituted or monosubstituted to trisubstituted by identical or different substituents selected from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, wherein the aryl moiety is unsubstituted or monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, wherein the aryl moiety is unsubstituted or monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, which is unsubstituted or monosubstituted to trisubstituted by identical or different substituents selected from the group consisting of halogen, alkyl having 1 to 4 carbon atom, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an unfused or benzo-fused, five- or six-membered heteroaromatic radical having 1 to 3 hetero atoms selected from the group consisting of sulphur and oxygen, which is unsubstituted or monosubstituted to trisubstituted by identical or different substituents selected from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms selected from the group consisting of fluorine and chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano, and $R^3$ represents straight-chain or branched alkyl having 1 to 6 carbon atoms, which is unsubstituted or monosubstituted to tetrasubstituted by identical or different substituents selected from the group consisting of halogen, alkoxy having 1 to 4 carbon atoms, alkoximino having 1 to 4 carbon atoms in the alkoxy moiety and cycloalkyl having 3 to 7 carbon atoms, or represents cycloalkyl having 3 to 7 carbon atoms, which is unsubstituted or monosubstituted to trisubstituted by identical or different substituents selected from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, wherein the aryl moiety is unsubstituted or monosubstituted to trisubstituted by identical or different substituents selected from the group consisting of halogen atoms, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, wherein the aryl moiety is unsubstituted or monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, which is unsubstituted or monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an unfused or benzo-fused, five- or six-membered heteroaromatic radical having 1 to 3 hetero atoms selected from the group consisting of nitrogen, sulphur and oxygen, which is unsubstituted or monosubstituted to trisubstituted by identical or different substituents selected from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano, or its acid addition salts or metal salt complexes.

2. A mercapto-imidazole compound of the formula (I-1)

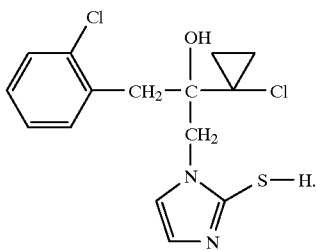

(I-1)

3. A process for the preparation of a mercapto-imidazolyl compound of the formula (I) of claim 1, or of its acid addition salts or metal salt complexes, comprising the steps of reacting an imidazole of the formula (II)

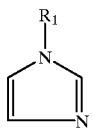

(II)

wherein
$R^1$ is as defined in claim 1, either
a) in succession with a strong base and sulphur in the presence of a diluent, and then hydrolyzing the product with water, or
b) with sulphur in the presence of a diluent having a high boiling point; and reacting the product of variant a) or b) of the formula (Ia)

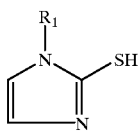

(Ia)

wherein
$R^1$ is as defined in claim 1,
with a halogen compound of the formula (III)

$$R^{16}\text{—Hal}$$

wherein
$R^{16}$ represents an alkyl having 1 to 4 carbon atoms, and
Hal represents chlorine, bromine or iodine,
in the presence of an acid binder and in the presence of a diluent.

4. The process of claim 3 wherein the reaction in variant a) is carried out in th, presence of an acid.

5. The process of claim 3 wherein variant b) further comprises the step of hydrolyzing the product with water.

6. The process of claim 3 wherein variant b) further comprises the step of hydrolyzing the product with an acid.

7. A microbicidal composition comprising a microbicidally effective amount of a compound or its acid addition salt or metal salt complex as claimed in claim 1 and an inert diluent.

8. A method for controlling undesired microorganisms in plant protection and in the preservation of materials, which method comprises applying to such undesired microorganisms or to their habitat a microbicidally effective amount of a compound or its acid addition salt or metal salt complex as claimed in claim 1.

9. The process of claim 3 further comprising the step of reacting the compounds of the formula (I) with an acid or a metal salt.

* * * * *